(12) United States Patent
Warlick et al.

(10) Patent No.: US 11,771,620 B2
(45) Date of Patent: Oct. 3, 2023

(54) ACOUSTIC SHOCK WAVE THERAPEUTIC METHODS TO PREVENT OR TREAT OPIOID ADDICTION

(71) Applicant: SoftWave Tissue Regeneration Technologies, LLC, Kennesaw, GA (US)

(72) Inventors: John F. Warlick, Woodstock, GA (US); John Patrick Finney, Hagerhill, KY (US)

(73) Assignee: Softwave Tissue Regeneration Technologies, LLC, Kennesaw, GA (US)

( * ) Notice: Subject to any disclaimer, the term of this patent is extended or adjusted under 35 U.S.C. 154(b) by 0 days.

(21) Appl. No.: 17/752,196

(22) Filed: May 24, 2022

(65) Prior Publication Data

US 2022/0280373 A1    Sep. 8, 2022

Related U.S. Application Data

(60) Division of application No. 16/353,278, filed on Mar. 14, 2019, now Pat. No. 11,389,373, which is a
(Continued)

(51) Int. Cl.
*A61H 23/00* (2006.01)
*A61H 39/00* (2006.01)
(Continued)

(52) U.S. Cl.
CPC .......... *A61H 23/008* (2013.01); *A61H 39/00* (2013.01); *A61M 19/00* (2013.01); *G10K 15/043* (2013.01);
(Continued)

(58) Field of Classification Search
CPC ...... A61H 23/008; A61H 39/00; A61H 23/02; A61H 2201/0153; A61H 2201/1635;
(Continued)

(56) References Cited

U.S. PATENT DOCUMENTS 5,727,556 A * 3/1998 Weth .................. A61N 5/02
607/46
9,974,519 B1 * 5/2018 Schwarz .............. A61B 8/0858
(Continued)

FOREIGN PATENT DOCUMENTS

DE          19721218 A1 * 11/1998 ........... A61H 23/008

OTHER PUBLICATIONS

English translation for DE 19721218, machine translated by Search Clarivate Analytics, translated on Mar. 2, 2023.*
(Continued)

*Primary Examiner* — Tu A Vo
(74) *Attorney, Agent, or Firm* — David L. King

(57) ABSTRACT

The method of treating a patient addicted to pain medication or opioids has the step administering acoustic shock waves or pressure pulses to the patient. A second embodiment includes a treatment to reduce a patient's pain caused by a medical condition and/or medical procedure to reduce or eliminate the taking of addictive pain medication. The treatment has the step of administering acoustic shock waves or pressure pulses directed to an area near a source of the pain or to one or more reflexology zones or to one or more reflexology zones and to an area near the source of the pain or both to treat the medical condition or prior to the medical procedure or during the medical procedure or after the medical procedure or any combination thereof.

4 Claims, 13 Drawing Sheets

Related U.S. Application Data continuation-in-part of application No. 16/009,807, filed on Jun. 15, 2018, now Pat. No. 11,389,372, which is a continuation-in-part of application No. 15/984,505, filed on May 21, 2018, now Pat. No. 11,389,371, and a continuation-in-part of application No. 15/131,303, filed on Apr. 18, 2016, now Pat. No. 11,389,370.

(60) Provisional application No. 62/730,608, filed on Sep. 13, 2018, provisional application No. 62/687,528, filed on Jun. 20, 2018.

(51) Int. Cl.
*A61M 19/00* (2006.01)
*G10K 15/04* (2006.01)
*A61M 21/02* (2006.01)
*A61H 23/02* (2006.01)
*A61M 21/00* (2006.01)
*A61B 5/00* (2006.01)

(52) U.S. Cl.
CPC ............ *A61B 5/4815* (2013.01); *A61H 23/02* (2013.01); *A61H 2201/0153* (2013.01); *A61H 2201/164* (2013.01); *A61H 2201/1635* (2013.01); *A61H 2201/1654* (2013.01); *A61H 2201/50* (2013.01); *A61H 2205/027* (2013.01); *A61H 2205/065* (2013.01); *A61H 2205/12* (2013.01); *A61H 2205/125* (2013.01); *A61M 21/02* (2013.01); *A61M 2021/0022* (2013.01)

(58) Field of Classification Search
CPC ...... A61H 2201/164; A61H 2201/1654; A61H 2201/50; A61H 2205/027; A61H 2205/065; A61H 2205/12; A61H 2205/125; A61M 19/00; A61M 21/02; A61M 2021/0022; G10K 15/043; A61B 5/4815

See application file for complete search history.

(56) References Cited

U.S. PATENT DOCUMENTS

| | | | |
|---|---|---|---|
| 2006/0036194 A1* | 2/2006 | Schultheiss | A61H 23/008 601/2 |
| 2006/0100552 A1* | 5/2006 | Schultheiss | A61H 23/008 601/2 |
| 2007/0142753 A1* | 6/2007 | Warlick | A61N 7/00 601/2 |
| 2011/0034832 A1* | 2/2011 | Cioanta | A61B 17/22029 601/1 |
| 2013/0211294 A1* | 8/2013 | Bohris | A61H 23/008 601/4 |
| 2013/0345600 A1* | 12/2013 | Katragadda | A61B 17/225 601/4 |
| 2017/0106201 A1* | 4/2017 | Schwarz | A61N 5/0625 |
| 2019/0201705 A1* | 7/2019 | Schwarz | A61N 5/0624 |

OTHER PUBLICATIONS

Yoon, "Effect of extracorporeal shock wave therapy on scar pain in burn patients", Medicine, Apr. 2016.*

* cited by examiner

ACOUSTIC SHOCK WAVE THERAPEUTIC METHODS TO PREVENT OR TREAT OPIOID ADDICTION

RELATED APPLICATIONS

The present invention is a division of U.S. Ser. No. 16/353,278 filed on Mar. 14, 2019 which is a continuation in part of co-pending U.S. application Ser. No. 16/009,807 filed Jun. 15, 2018 entitled, "Improved Acoustic Shock Wave Therapeutic Methods" which is a continuation in part of applications U.S. Ser. No. 15/984,505 entitled "Improved Acoustic Shock Wave Therapeutic Methods" filed on May 21, 2018 and U.S. Ser. No. 15/131,303 entitled "Treatments For Blood Sugar Levels And Muscle Tissue Optimization Using Extracorporeal Acoustic Shock Waves" filed on Apr. 18, 2016.

TECHNICAL FIELD

The present invention relates to an improved pre-treatment method of utilizing acoustic shock waves or pressure pulses to reduce pain after a medical procedure and thereby reduce the need for prescribing addictive dosages of pain medications and a post treatment method to overcome opioid addictions.

BACKGROUND OF THE INVENTION

In U.S. Pat. No. 7,470,240 B2, entitled "Pressure Pulse/Shock Wave Therapy Methods And An Apparatus For Conducting The Therapeutic Methods", is disclosed a novel use of unfocused shock waves to stimulate a cellular substance. From this patent a family of treatment patents evolved. The list includes U.S. Pat. Nos. 7,841,995; 7,883,482; 7,905,845 all divisional applications; and U.S. Pat. No. 7,507,213 entitled "Pressure Pulse/Shock Wave Therapy Methods For Organs"; U.S. Pat. No. 7,544,171 B2 entitled "Methods for Promoting Nerve Regeneration and Neuronal Growth and Elongation"; U.S. Pat. No. 7,988,648 B2 entitled "Pancreas Regeneration Treatment For Diabetics Using Extracorporeal Acoustic shock waves or pressure pulses"; all teaching a new useful way to deliver acoustic shock waves or pressure pulses to achieve a healing response. Each of these patents are incorporated herein by reference in their entirety. In addition, patents U.S. Pat. Nos. 8,257,282 and 8,535,249 for the device to perform these methods by delivering low energy unfocused acoustic shock waves or pressure pulses to the cellular tissue being treated.

During this inventive research, the inventors disclosed the use of acoustic shock waves or pressure pulses could be beneficial as a disease preventative therapy of at risk patients to such ailments as heart disease and other conditions.

While this large volume of research has been rewarded by the granting of numerous patents, much new work has been evolving as the understanding of the technology is being applied. It is in this latest work that some, heretofore, unknown improvements and refinements have been discovered that were hidden from and unappreciated by scientists in this field. In particular, the use of acoustic shock waves or pressure pulses to regulate and in some cases stimulate glandular hormonal secretions or modulate glandular hormonal secretions.

In recently filed co-pending U.S. patent application Ser. No. 15/984,505 filed May 21, 2018 entitled "Improved Acoustic Shock Wave Therapeutic Methods" which is also being incorporated herein by reference in its entirety discloses a method of modulating glandular secretions by administering acoustic shock waves or pressure pulses to a gland, includes the steps of activating acoustic shock waves or pressure pulses of an acoustic shock wave or pressure pulse generator to emit acoustic shock waves or pressure pulses and subjecting the gland to acoustic shock waves or pressure pulses stimulating the gland to have a modulated response. The modulated response is one of an adjustment in hormonal release which increases low level output, decreases high level output or stabilizes erratic output.

This evolved into a method of modulating glandular secretions by administering acoustic shock waves or pressure pulses to one or more reflexology zones or to one or more reflexology zones and to an area near the source of the pain or region has been discovered. In one preferred embodiment, a treatment method achieves one or more of a) modulating blood sugar levels, b) stimulating insulin production levels or c) normalizing A1C levels by using the step of administering acoustic shock waves or pressure pulses to one or more reflexology zones or to one or more reflexology zones and to an area near the source of the pain or region. This treatment method, U.S. application Ser. No. 16/009,807 filed on Jun. 15, 2018 entitled "Improved Acoustic Shock Wave Therapeutic Methods" is also incorporated herein by reference in its entirety.

These most recent inventions have recently and quite unexpectedly discovered an improved treatment therapy that achieves all the objectives of the earlier work in a newly discovered and remarkably efficient way which directs acoustic shock waves or pressure pulses to reflexology regions to achieve a desired response.

The present invention has built upon this large volume of work with a discovery that a pre-treatment of acoustic shock wave therapy prior to any medical procedure or optionally during such a procedure will reduce the patient's post treatment requirement for addictive pain medications such as "opioids" and other addictive pain medications. Further, the ability of acoustic shock waves or pressure pulses to reduce pain allows this shock wave therapy to be used to overcome addictions in patients already addicted as is described below.

By the turn of the 19th century, it was agreed that the stimulation of sympathetic nerves could cause different effects on body tissues, depending on the conditions of stimulation (such as the presence or absence of some toxin). Over the first half of the 20th century, two main proposals were made to explain this phenomenon: There were (at least) two different types of neurotransmitters released from sympathetic nerve terminals, or There were (at least) two different types of detector mechanisms for a single neurotransmitter.

The first hypothesis was championed by Walter Bradford Cannon and Arturo Rosenblueth, who interpreted many experiments to then propose that there were two neurotransmitter substances, which they called sympathin E (for 'excitation') and sympathin I (for 'inhibition'). The second hypothesis found support from 1906 to 1913, when Henry Hallett Dale explored the effects of adrenaline (which he called adrenine at the time), injected into animals, on blood pressure. Usually, adrenaline would increase the blood pressure of these animals Although, if the animal had been exposed to ergotoxine, the blood pressure decreased. He proposed that the ergotoxine caused "selective paralysis of motor myoneural junctions" (i.e. those tending to increase the blood pressure) hence revealing that under normal conditions that there was a "mixed response", including a mechanism that would relax smooth muscle and cause a fall in blood pressure. This "mixed response", with the same compound causing either contraction or relaxation, was conceived of as the response of different types of junctions to the same compound.

This line of experiments was developed by several groups, including DT Marsh and colleagues, who in February 1948 showed that a series of compounds structurally related to adrenaline could also show either contracting or relaxing effects, depending on whether or not other toxins were present. This again supported the argument that the muscles had two different mechanisms by which they could respond to the same compound. In June of that year, Raymond Ahlquist, Professor of Pharmacology at Medical College of Georgia, published a paper concerning adrenergic nervous transmission. In it, he explicitly named the different responses as due to what he called α receptors and β receptors, and that the only sympathetic transmitter was adrenaline. While the latter conclusion was subsequently shown to be incorrect (it is now known to be noradrenaline), his receptor nomenclature and concept of two different types of receptor mechanisms for a single neurotransmitter, remains. In 1954, he was able to incorporate his findings in a textbook, Drill's Pharmacology in Medicine, and thereby promulgate the role played by α and β receptor sites in the adrenaline/noradrenaline cellular mechanism. These concepts would revolutionize advances in pharmacotherapeutic research, allowing the selective design of specific molecules to target medical ailments rather than rely upon traditional research into the efficacy of pre-existing herbal medicines.

The present invention has been demonstrated to be able to modulate these receptors in a unique way in the absence of pharmaceutical drugs such as inhibitors.

SUMMARY OF THE INVENTION

The present invention immediately shuts down the inflammatory response at the treatment site. This has been linked to modulation of various signaling molecules, including TLR3, NO, ATP, microvesicles and exosomes. Results are typically immediate and sustained relief of chronic pain. The present invention sustainingly improves blood flow. This has been linked to the release of vascular endothelial growth factor (VEGF) and other key growth factors and cytokines, as well as a boost in ATP, leading to neo angio/vasculogenesis at the treatment site, typically resulting in accelerated and sustaining regenerative effect. The shock waves and pressure pulses of the present invention technology is scientifically validated to recruit and activate endogenous stem cells and elicit biofeedback by which "origins of pain" can be precisely identified, serving an invaluable role in treatment effectiveness and efficiency.

A treatment method to reduce a patient's pain caused by a medical condition and/or medical procedure to reduce or eliminate the taking of addictive pain medication is disclosed. The treatment has the step of administering acoustic shock waves or pressure pulses directed to one or more reflexology zones or to one or more reflexology zones and to an area near the source of the pain to treat the medical condition or prior to the medical procedure or during the medical procedure or after the medical procedure or any combination thereof. The treatment further has the steps of activating acoustic shock waves or pressure pulses of an acoustic shock wave or pressure pulse generator to emit acoustic shock waves or pressure pulses and subjecting the one or more reflexology zones or the one or more reflexology zones and an area near the source of the pain to acoustic shock waves or pressure pulses stimulating the one or more reflexology zones or the one or more reflexology zones and an area near the source of the pain to have a modulated response wherein the modulated response is one or more of reducing patient anxiety by stimulating or modulating alpha and/or Beta adrenergic receptors to control and reduce high stress and anxiety or suppressing pain or activating an anesthetic effect over a period of time. Additionally, the treatment further has the step of recruiting, activating and differentiating stem cells by directly targeting the pathologic tissue or by targeting the reflexology zones or doing both. Further, additionally, the treatment further has the step of modulating inflammation locally by a direct targeting, or by modulating systemic inflammation by treating any or all of the reflexology zones, or by doing both. The emitted acoustic shock waves or pressure pulses can be focused or unfocused acoustic shock waves or pressure pulses.

The reflexology zones are located in a region of a foot or hand or ear of the patient. The shock wave or pressure pulse generator is acoustically coupled to the patient's skin using a coupling gel or liquid. The treatment method wherein the treatment reduces or eliminates systemic or local inflammation. The treatment method wherein the treatment initiates, activates or recruits stem cells. The treatment method wherein the treatment reduces or eliminates systemic or local inflammation and initiates, activates or recruits stem cells.

Stimulating the one or more reflexology zones or the one or more reflexology zones and the area near a source of the medical condition or pain causes a stimulation or modulation of adrenergic receptors a and p and one or more of a release of nitric oxide, secretion of digestive enzymes, hormones and other fluids and can cause a release of growth factors including, but not limited to vascular endothelial growth factor (VEGF), can also cause new blood vessels to be created increasing vascularization. Stimulating the one or more reflexology zones or the one or more reflexology zones and the area near a source of the medical condition or pain also modulates and/or stimulates the adrenergic alpha and beta receptors to reduce and control a patient's stress and anxiety to calm patients reducing or eliminating pharmacologic compositions such as serotonin uptake inhibitors and to facilitate treating pain drug addicted patients by reducing withdrawal symptoms. The treatment method can be repeated one or more times prior to or during the medical procedure or after the medical procedure. The emitted acoustic shock waves or pressure pulses can be low energy soft waves wherein the low energy soft waves have an energy density in the range of 0.01 mJ/mm$^2$ to 1.0 mJ/mm$^2$, preferably in the range of 0.04 mJ/mm$^2$ to 0.3 mJ/mm$^2$. Each subjected reflexology zone receives between 100 and 100,000 acoustic shock waves or pressure pulses per therapy session. The emitted acoustic shock waves or pressure pulses are spherical, radial, convergent, divergent, planar, near planar, focused or unfocused from a source with or without a lens that is one of electrohydraulic, electromagnetic, piezoelectric, ballistic or water jets configured to produce an acoustic shock wave and wherein the acoustic shock waves or pressure pulses are administered invasively or noninvasively. Ideally, number of repeated treatments occur on a schedule over a period of three or more weeks, and treatments can be repeated over time as a pain prevention protocol over longer durations of time between repeated treatments.

An important embodiment has a method of treating a patient addicted to pain medication. This method has the step of administering acoustic shock waves or pressure pulses to the patient exhibiting an addiction to pain medications or opioids wherein the administering of acoustic shock waves or pressure pulses occurs at a location of one or more reflexology zones or to one or more reflexology zones and to an area near the source of the pain at an extremity of the hands or the feet or the ears. The method allows the patient with the addiction to have a reduction in chronic pain. The method further has the steps of activating acoustic shock waves or pressure pulses of an acoustic shock wave or pressure pulse generator to emit acoustic shock waves or pressure pulses; subjecting the location to acoustic shock waves or pressure pulses stimulating the one or more reflexology zones or the one or more reflexology zones and the area near a source of the medical condition or pain to have a modulated response wherein the modulated response is one or more of reducing patient anxiety or suppressing pain or activating an anesthetic effect over a period of time; and wherein the emitted acoustic shock waves or pressure pulses are focused or unfocused acoustic shock waves or pressure pulses. The administration of emitted shock waves is additionally directed to the one or more reflexology zones or the one or more reflexology zones and the area near a source of the medical condition or pain to modulate a response to the pain to suppress urges to take the addictive medication or opioids and to minimize withdrawal symptoms. The treatment further allows substituting prescribed addictive medications or opioids with non or less additive medications.

Definitions

"A1C level": refers to the Hemoglobin Ale (HbA1c) Test for Diabetes. The hemoglobin Ale test measures average blood glucose over the past 2 to 3 months. It's also called HbA1c, glycated hemoglobin test, and glycohemoglobin. People who have diabetes need this test regularly to see if their levels are staying within range. It is used to determine if there is a need to adjust a person's diabetes medicines. The A1C test is also used to diagnose diabetes.

"Adrenal Gland": The adrenal glands (also known as suprarenal glands) are endocrine glands that produce a variety of hormones including adrenaline and the steroids aldosterone and cortisol. They are found above the kidneys. Each gland has an outer cortex which produces steroid hormones and an inner medulla.

"Adrenaline": Adrenaline, also known as adrenalin or epinephrine, is a hormone, neurotransmitter, and medication. Epinephrine is normally produced by both the adrenal glands and certain neurons. It plays an important role in the fight-or-flight response by increasing blood flow to muscles, output of the heart, pupil dilation, and blood sugar.

"Adrenergic receptor", the adrenergic receptors or adrenoceptors are a class of G protein-coupled receptors that are targets of many catecholamines like norepinephrine (noradrenaline) and epinephrine (adrenaline) produced by the body, but also many medications like beta blockers, P2 agonists and a2 agonists, which are used to treat high blood pressure and asthma for example. Many cells have these receptors, and the binding of a catecholamine to the receptor will generally stimulate the sympathetic nervous system (SNS). SNS is responsible for the fight-or-flight response, which is triggered for example by exercise or fear causing situations. This response dilates pupils, increases heart rate, mobilizes energy, and diverts blood flow from non-essential organs to skeletal muscle. These effects together tend to increase physical performance momentarily.

"Aldosterone": Aldosterone, the main mineralocorticoid hormone, is a steroid hormone produced by the zona glomerulosa of the adrenal cortex in the adrenal gland. It is essential for sodium conservation in the kidney, salivary glands, sweat glands and colon. It plays a central role in the homeostatic regulation of blood pressure, plasma sodium (Na+), and potassium (K+) levels. It does so mainly by acting on the mineralocorticoid receptors in the distal tubules and collecting ducts of the nephron. It influences the reabsorption of sodium and excretion of potassium (from and into the tubular fluids, respectively) of the kidney, thereby indirectly influencing water retention or loss, blood pressure and blood volume. When dysregulated, aldosterone is pathogenic and contributes to the development and progression of cardiovascular and renal disease.

"Blood sugar level": The blood sugar level, blood sugar concentration, or blood glucose level is the amount of glucose present in the blood of humans and other animals Glucose is a simple sugar and approximately 4 grams of glucose are present in the blood of a 70-kilogram (150 lb) human at all times. The body tightly regulates blood glucose levels as a part of metabolic homeostasis. Glucose is stored in skeletal muscle and liver cells in the form of glycogen; in fasted individuals, blood glucose is maintained at a constant level at the expense of glycogen stores in the liver and skeletal muscle. Cellular glucose uptake is primarily regulated by insulin, a hormone produced in the pancreas. Blood sugar levels outside the normal range may be an indicator of a medical condition. A persistently high level is referred to as hyperglycemia; low levels are referred to as hypoglycemia.

"Cortisol": Cortisol is a steroid hormone, in the glucocorticoid class of hormones. When used as a medication, it is known as hydrocortisone. It is produced in humans by the zona fasciculata of the adrenal cortex within the adrenal gland. It is released in response to stress and low blood-glucose concentration. It functions to increase blood sugar through gluconeogenesis, to suppress the immune system, and to aid in the metabolism of fat, protein, and carbohydrates. It also decreases bone formation.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Estrogen": A female steroid hormone that is produced by the ovaries and, in lesser amounts, by the adrenal cortex, placenta, and male testes. Estrogen helps control and guide sexual development, including the physical changes associated with puberty. It also influences the course of ovulation in the monthly menstrual cycle, lactation after pregnancy, aspects of mood, and the aging process. Production of estrogen changes naturally over the female lifespan, reaching adult levels with the onset of puberty (menarche) and decreasing in middle age until the onset of menopause. Estrogen deficiency can lead to lack of menstruation (amenorrhea), persistent difficulties associated with menopause (such as mood swings and vaginal dryness), and osteoporosis in older age. In cases of estrogen deficiency, natural and synthetic estrogen preparations may be prescribed. Estrogen is also a component of many oral contraceptives. An overabundance of estrogen in men causes development of female secondary sexual characteristics (feminization), such as enlargement of breast tissue.

"extracorporeal" means occurring or based outside the living body.

A "generalized paraboloid" according to the present invention is also a three-dimensional bowl. In two dimensions (in Cartesian coordinates, x and y) the formula yn=2px [with n being i−2, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p (−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"Hormone": A hormone is any member of a class of signaling molecules produced by glands in multicellular organisms that are transported by the circulatory system to target distant organs to regulate physiology and behaviour. Hormones have diverse chemical structures, mainly of 3 classes: eicosanoids, steroids, and amino acid/protein derivatives (amines, peptides, and proteins). The glands that secrete hormones comprise the endocrine signaling system. The term hormone is sometimes extended to include chemicals produced by cells that affect the same cell (autocrine or intracrine signalling) or nearby cells (paracrine signalling). Hormones are used to communicate between organs and tissues for physiological regulation and behavioral activities, such as digestion, metabolism, respiration, tissue function, sensory perception, sleep, excretion, lactation, stress, growth and development, movement, reproduction, and mood. Hormones affect distant cells by binding to specific receptor proteins in the target cell resulting in a change in cell function. When a hormone binds to the receptor, it results in the activation of a signal transduction pathway that typically activates gene transcription resulting in increased expression of target proteins; non-genomic effects are more rapid, and can be synergistic with genomic effects Amino acid-based hormones (amines and peptide or protein hormones) are water-soluble and act on the surface of target cells via second messengers; steroid hormones, being lipid-soluble, move through the plasma membranes of target cells (both cytoplasmic and nuclear) to act within their nuclei. Hormone secretion may occur in many tissues. Endocrine glands are the cardinal example, but specialized cells in various other organs also secrete hormones. Hormone secretion occurs in response to specific biochemical signals from a wide range of regulatory systems. For instance, serum calcium concentration affects parathyroid hormone synthesis; blood sugar (serum glucose concentration) affects insulin synthesis; and because the outputs of the stomach and exocrine pancreas (the amounts of gastric juice and pancreatic juice) become the input of the small intestine, the small intestine secretes hormones to stimulate or inhibit the stomach and pancreas based on how busy it is. Regulation of hormone synthesis of gonadal hormones, adrenocortical hormones, and thyroid hormones is often dependent on complex sets of direct influence and feedback interactions involving the hypothalamic-pituitary-adrenal (HPA), -gonadal (HPG), and -thyroid (HPT) axes. Upon secretion, certain hormones, including protein hormones and catecholamines, are water-soluble and are thus readily transported through the circulatory system. Other hormones, including steroid and thyroid hormones, are lipid-soluble; to allow for their widespread distribution, these hormones must bond to carrier plasma glycoproteins (e.g., thyroxine-binding globulin (TBG)) to form ligand-protein complexes. Some hormones are completely active when released into the bloodstream (as is the case for insulin and growth hormones), while others are prohormones that must be activated in specific cells through a series of activation steps that are commonly highly regulated. The endocrine system secretes hormones directly into the bloodstream typically into fenestrated capillaries, whereas the exocrine system secretes its hormones indirectly using ducts. Hormones with paracrine function diffuse through the interstitial spaces to nearby target tissue.

"Hypothalamus": The hypothalamus is a portion of the brain that contains a number of small nuclei with a variety of functions. One of the most important functions of the hypothalamus is to link the nervous system to the endocrine system via the pituitary gland (hypophysis). The hypothalamus is located below the thalamus and is part of the limbic system.

"Insulin": is a hormone made by the pancreas that allows your body to use sugar, glucose, from carbohydrates in the food that is eaten for energy or to store glucose for future use. Insulin helps keeps blood sugar levels from getting too high (hyperglycemia) or too low (hypoglycemia).

"Melatonin": Melatonin, also known as N-acetyl-5-methoxy tryptamine, is a hormone that is produced by the pineal gland in animals and regulates sleep and wakefulness. In animals, melatonin is involved in the entrainment (synchronization) of the circadian rhythms including sleep-wake timing, blood pressure regulation, seasonal reproduction, and many others. Many of its biological effects in animals are produced through activation of melatonin receptors, while others are due to its role as an antioxidant, with a particular role in the protection of nuclear and mitochondrial DNA.

A "paraboloid" according to the present invention is a three-dimensional reflecting bowl. In two dimensions (in Cartesian coordinates, x and y) the formula y2=2px, wherein p/2 is the distance of the focal point of the paraboloid from its apex, defines the paraboloid. Rotation of the two-dimensional figure defined by this formula around its longitudinal axis generates a de facto paraboloid.

"Parathyroid": Parathyroid glands are small endocrine glands in the neck of humans and other tetrapods that produce parathyroid hormone. Humans usually have four parathyroid glands, variably located on the back of the thyroid gland. Parathyroid hormone and calcitonin (one of the hormones made by the thyroid gland) have key roles in regulating the amount of calcium in the blood and within the bones.

"Parathyroid Hormone": Parathyroid hormone (PTH) also called parathormone or parathyrin, is a hormone secreted by the parathyroid glands that is important in bone remodeling, which is an ongoing process in which bone tissue is alternately resorbed and rebuilt over time. PTH is secreted in response to low blood serum calcium (Ca2+) levels. PTH indirectly stimulates osteoclast activity within bone marrow, in an effort to release more ionic calcium (Ca2+) into the blood to elevate serum calcium (Ca2+) levels. The bones act as a (metaphorical) "bank of calcium" from which the body can make "withdrawals" as needed to keep the amount of calcium in the blood at appropriate levels despite the ever-present challenges of metabolism, stress, and nutritional variations. PTH is "a key that unlocks the bank vault" to remove the calcium. In consequence, PTH is vital to health, and health problems that yield too little or too much PTH (such as hypoparathyroidism, hyperparathyroidism, or paraneoplastic syndromes) can wreak havoc in the form of bone disease, hypocalcaemia, and hypercalcaemia.

"Pineal body": Pineal gland, also called conarium, epiphysis cerebri, pineal organ, or pineal body, endocrine gland. The pineal gland is a small endocrine gland in the vertebrate brain. The pineal gland produces melatonin, a serotonin-derived hormone which modulates sleep patterns in both circadian and seasonal cycles. The shape of the gland resembles a pine cone, hence its name The pineal gland is located in the epithalamus, near the center of the brain, between the two hemispheres, tucked in a groove where the two halves of the thalamus join.

"Pituitary gland": In vertebrate anatomy, the pituitary gland, or hypophysis, is an endocrine gland about the size of a pea and weighing 0.5 grams (0.018 oz) in humans. It is a protrusion off the bottom of the hypothalamus at the base of the brain. The hypophysis rests upon the hypophysial fossa of the sphenoid bone in the center of the middle cranial fossa and is surrounded by a small bony cavity (sella turcica) covered by a dural fold (diaphragma sellae). The anterior pituitary (or adenohypophysis) is a lobe of the gland that regulates several physiological processes (including stress, growth, reproduction, and lactation). The intermediate lobe synthesizes and secretes melanocyte-stimulating hormone. The posterior pituitary (or neurohypophysis) is a lobe of the gland that is functionally connected to the hypothalamus by the median eminence via a small tube called the pituitary stalk (also called the infundibular stalk or the infundibulum). Hormones secreted from the pituitary gland help control: growth, blood pressure, management of energy, all functions of the sex organs, thyroid glands and metabolism as well as some aspects of pregnancy, childbirth, nursing, water/salt concentration at the kidneys, temperature regulation and pain relief.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milliseconds (ms). Very fast pressure pulses are called shock waves. Shock waves used in medical applications do have amplitudes above 0.1 MPa and rise times of the amplitude can be below 1000 ns, preferably at or below 100 ns. The duration of a shock wave is typically below 1-3 microseconds (µs) for the positive part of a cycle and typically above some micro-seconds for the negative part of a cycle.

"Reflexology zone" as used herein means an area or pressure point on the feet or hands that are access pathways to every organ, gland, muscle, etc. These pathways between pressure points and other parts of the body are thought to be connected via the nervous system and that a neurological relationship exists between the skin and the internal organs, and that the whole nervous system adjusts to a stimulus. According to reflexology theory, application of pressure to feet, hands, or ears sends a calming message from the peripheral nerves in these extremities to the central nervous system, which in turn signals the body to adjust the tension level. This enhances overall relaxation, removes stress, brings internal organs and their systems into a state of optimum functioning, and increases blood supply which brings additional oxygen and nutrients to cells and enhances waste removal. It positively affects the circulatory, respiratory, endocrine, immune, and neuropeptide systems in the body.

"Reproductive glands" include ovaries and testes: A woman's 2 ovaries are located on each side of the uterus, just below the opening of the fallopian tubes (tubes that extend from the uterus to near the ovaries). The ovaries contain the egg cells needed for reproduction. They also make estrogen and progesterone. These affect many of the female characteristics and reproductive functions. Estrogens also play an important role in bone health and strength. The levels of estrogen and progesterone are controlled by certain hormones made by the pituitary gland. The testes are oval-shaped organs that hang suspended in a pouch of skin (scrotum) outside the male body. The testes are the site of sperm production. They also make testosterone and other hormones. These affect many of the male characteristics and support sperm production. Testosterone also plays an important role in bone health and strength.

"Shock Wave": As used herein is defined by Camilo Perez, Hong Chen, and Thomas J. Matula; Center for Industrial and Medical Ultrasound, Applied Physics Laboratory, University of Washington, 1013 NE 40th Street, Seattle, Washington 98105; Maria Karzova and Vera A. Khokhlovab; Department of Acoustics, Faculty of Physics, Moscow State University, Moscow 119991, Russia; (Received 9 Oct. 2012; revised 16 Apr. 2013; accepted 1 May 2013) in their publication, "Acoustic field characterization of the Duolith: Measurements and modeling of a clinical shock wave therapy device"; incorporated by reference herein in its entirety.

"Testosterone": Testosterone is the primary male sex hormone and an anabolic steroid. In male humans, testosterone plays a key role in the development of male reproductive tissues such as testes and prostate, as well as promoting secondary sexual characteristics such as increased muscle and bone mass, and the growth of body hair. In addition, testosterone is involved in health and well-being, and the prevention of osteoporosis. Insufficient levels of testosterone in men may lead to abnormalities including frailty and bone loss. Testosterone is a steroid from the androstane class containing a keto and hydroxyl groups at the three and seventeen positions respectively. It is biosynthesized in several steps from cholesterol and is converted in the liver to inactive metabolites. It exerts its action through binding to and activation of the androgen receptor. In humans and most other vertebrates, testosterone is secreted primarily by the testicles of males and, to a lesser extent, the ovaries of females. On average, in adult males, levels of testosterone are about 7 to 8 times as great as in adult females. As the metabolism of testosterone in males is greater, the daily production is about 20 times greater in men. Females are also more sensitive to the hormone.

"Thymus": The thymus is a specialized primary lymphoid organ of the immune system. Within the thymus, T cells mature. T cells are critical to the adaptive immune system, where the body adapts specifically to foreign invaders. The thymus is composed of two identical lobes and is located anatomically in the anterior superior mediastinum, in front of the heart and behind the sternum. Histologically, each lobe of the thymus can be divided into a central medulla and a peripheral cortex which is surrounded by an outer capsule. The cortex and medulla play different roles in the development of T cells. Cells in the thymus can be divided into thymic stromal cells and cells of hematopoietic origin (derived from bone marrow resident hematopoietic stem cells). Developing T cells are referred to as thymocytes and are of hematopoietic origin. Stromal cells include epithelial cells of the thymic cortex and medulla, and dendritic cells. The thymus provides an inductive environment for development of T cells from hematopoietic progenitor cells. In addition, thymic stromal cells allow for the selection of a functional and self-tolerant T cell repertoire. Therefore, one of the most important roles of the thymus is the induction of central tolerance. The thymus is largest and most active during the neonatal and pre-adolescent periods. By the early teens, the thymus begins to atrophy and thymic stroma is mostly replaced by adipose (fat) tissue. Nevertheless, residual T lymphopoiesis continues throughout adult life.

"Thyroid": The thyroid gland, or simply the thyroid, is an endocrine gland in the neck, consisting of two lobes connected by an isthmus. It is found at the front of the neck, below the Adam's apple. The thyroid gland secretes thyroid hormones, which primarily influence the metabolic rate and protein synthesis. The hormones also have many other effects including those on development. The thyroid hormones triiodothyronine (T3) and thyroxine (T4) are created from iodine and tyrosine. The thyroid also produces the hormone calcitonin, which plays a role in calcium homeostasis. Hormonal output from the thyroid is regulated by thyroid-stimulating hormone (TSH) secreted from the anterior pituitary gland, which itself is regulated by thyrotropin-releasing hormone (TRH) produced by the hypothalamus. The thyroid may be affected by several diseases. Hyperthyroidism occurs when the gland produces excessive amounts of thyroid hormones, the most common cause being Graves' disease, an autoimmune disorder. In contrast, hypothyroidism is a state of insufficient thyroid hormone production. Worldwide, the most common cause is iodine deficiency. Thyroid hormones are important for development, and hypothyroidism secondary to iodine deficiency remains the leading cause of preventable intellectual disability. In iodine-sufficient regions, the most common cause of hypothyroidism is Hashimoto's thyroiditis, also an autoimmune disorder. In addition, the thyroid gland may also develop several types of nodules and cancer.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1:
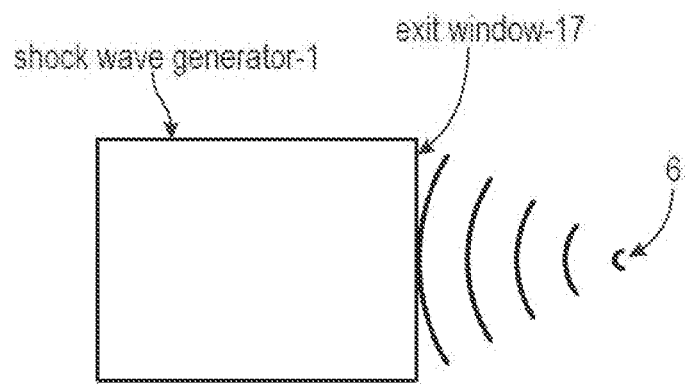
FIG. 1 is a simplified depiction of a pressure pulse I shock wave (PP/SW) generator with focusing wave characteristics.

The present methodology uses an acoustic shock wave form directed to specific reflexology zones to stimulate a modulated response. The present invention described herein teaches a therapy to reduce the number of opioid addictions following surgery by reducing the need for pain medication post-surgery; and, aiding in the recovery from addiction of pain medications and opioids by elimination chronic pain in the addict and minimizing the withdrawal symptoms in the addict.

The present inventors have treated hundreds of "addicts", those individuals suffering from prescription or opioid addiction, successfully including those patients who require pain medication and/or opiates daily to manage their pain such that a patient can participate in daily activities. A huge success rate is being achieved as they only treat those motivated patients who seek out treatment for their chronic injuries and want to get off pain medication or opiates. Two million new addicts are created annually following elective surgery in the USA. These people are target patients. Additionally, the present invention has had substantial success in treating long term addicts as well. This is especially true when an added incentive of a job treating other addicts is afforded with this technology upon the successful "kicking" of the addiction. This effort is part of a Kentucky project.

The inventors have also proven the ability to prevent long term chronic pain not only in their clinical experiences but in their published skin flap rat model. By treating the standardized skin flap of the mouse with shock waves they reduced the area of necrosis post-surgery by 75% and accelerated complete healing by 50%. This must translate into pain reduction and the need for pain meds. They treated the mouse a day prior to, or during surgery to reduce healing time and necrosis. This is the preferred embodiment. Treat a patient during surgery to (1) prevent adverse effects and prevent infection (2) reduce the recovery time and (3) reduce post-surgical pain. All 3 factor in long term pain medication usage. The advantage of treating during surgery is that treating a patient in the acute injury phase is painful. During surgery one can increase the energy level and the number of shocks to improve outcomes and reduce the amount of future pain medication, thus reducing the likelihood of addiction.

Treating the reflexology zones in both hands and feet of the addict can minimize the anxiety and pain during the withdrawal period and generally just make the addict feel better. The inventors have seen this in numerous cases and this is included in this patent.

In the extracorporeal shock wave or pressure pulse method of treating a patient, the administered shock waves or pressure pulses are directed to a treatment location or target site on the anatomy. In this invention, the term target site refers to either a location near the source of the medical condition or pain or to a reflexology location for a specific orthopedic bone structure, nerve, gland and the tissue of the hand or foot at the desired reflexology zone or region being in the path of the shock wave applicator. As used herein, "near" recognizes that the emitted shock waves or pressure pulses are transmitted through the skin and subcutaneous tissue directed toward the treatment location, preferably at or in close proximity to the treatment location or site. The patient is placed in a convenient orientation to permit the source of the emitted waves to most directly send the waves to the target site to initiate shock wave stimulation of the target area. Assuming the target area is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent or near planar and having a low-pressure amplitude and density in the range of 0.00001 $mJ/mm^2$ to 1.0 $mJ/mm^2$ or less, most typically below 0.2 $mJ/mm^2$. The focused source can use a focused beam of waves or can optionally use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission. Understanding the higher the energy used, the more sensation of pain the patient may experience.

These shock wave energy transmissions are effective in stimulating a cellular response and in some cases, such as unfocused low energy, and even low energy focused emissions can be accomplished without creating the localized hemorrhaging caused by rupturing cavitation bubbles in the tissue of the target site. This effectively insures the patient does not have to experience the sensation of pain so common in the higher energy focused wave forms having a focal point at or within the targeted treatment site. Higher energy acoustic shock waves or pressure pulses including focused ways can be used if the patient is adequately sedated such as during a surgical preparation or even during a surgical procedure.

Accordingly, unless for other reasons such as a trauma or immediate post-operative shock wave therapy no localized or general anesthesia is required. Post-operative shock wave therapy typically will be administered without such sedations at low energy.

If the target site is within the body, it may be such that the patient or the generating source must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments. Alternatively, the wave source generators may be deployed in an array wherein the subject patient is effectively enveloped or surrounded by a plurality of low energy wave source generators which can be simultaneously bombarding the target site from multiple directions.

The goal in such treatments is to provide 100 to 3000 acoustic shock waves or pressure pulses at a voltage of 14 kV to 28 kV across a spark gap generator in a single treatment preferably or one or more adjuvant treatments by targeting the site impinging the emitted waves on the desired reflexology target.

The present method, in many cases, does not rely on precise site location per se. The physician's general understanding of the anatomy of the patient should be sufficient to locate the reflexology target site to be treated. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating cellular release or activation of VEGF and other growth factors and most importantly to modulate and regulate hormonal secretions from a specific targeted gland by emitting waves to a desired reflexology zone. In other cases where the precise location must be known, the use of an applicator acoustic wave emission is directed by an ultrasound image, preferably the applicator has a software program coupled to the imaging device to allow the doctor to visualize the area being treated. The applicator can be hand held or manipulated in a fixture, if so desired, in either way the doctor can see the reflexology zone for any gland to be stimulated and the selected reflexology zone reflects the path of the wave transmission to modulate that bone structure, nerve or gland.

A key advantage of the present inventive methodology is that it is complimentary to conventional medical procedures. In the case of any other procedure, the area of the patient can be post operatively bombarded with these low energy waves to stimulate cellular release of healing agents and growth factors. Most preferably such patients may be provided more than one such ESWT treatment with an intervening dwell time for cellular relaxation prior to secondary and tertiary treatments.

The underlying principle of these shock wave therapy methods is to stimulate the body's own natural healing capability through the reflexology zone. This is accomplished by deploying shock waves to stimulate strong cells in the tissue to activate a variety of responses. The acoustic shock waves or pressure pulses transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced but also the number of applied shock wave impulses can be lowered from several thousand to as few as one or more pulses and still yield a beneficial stimulating response. This allows acoustic wave therapies to be directed to a specific reflexology zone directed toward, for example, an endocrine gland being treated with confidence the signal will be fed back to the entire system via the pituitary gland (hypophysis). This use of acoustic wave stimulation allows a therapy to be given to modulate and adjust glandular secretions of hormones to be regulated and adjusted to achieve a desired adjustment, for example if too low to increase specific secretions, if too high to lessen these secretions. Most importantly, the modulation of and reduction of pain can be achieved in the bone structure and nerves affected by a medical condition and/or medical procedure.

The biological model motivated the design of sources with low pressure amplitudes and energy densities. First: spherical waves generated between two tips of an electrode; and second: nearly even waves generated by generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends to the desired reflexology zone or site, preferably at or beyond the target reflexology treatment site within or even potentially external to the patient. In any event, the beam of acoustic waves transmitted needs to project in a large enough reflexology zone or area to stimulate or modulate the gland. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a reflexology treatment site or zone, generating either focused shock waves or unfocused shock waves, of directing these shock waves to the treatment site; and applying a sufficient number of these shock waves to induce activation of one or more growth factor thereby inducing or accelerating a modulated adjustment to achieve a proper regulated glandular, muscular, bone or nerve response.

The unfocused shock waves can be of a divergent wave pattern or near planar pattern preferably of a low peak pressure amplitude and density. Typically, the energy density values range as low as 0.000001 $mJ/mm^2$ and having a high end energy density of below 1.0 $mJ/mm^2$, preferably 0.40 $mJ/mm^2$ or less, more preferably 0.20 $mJ/mm^2$ or less. The peak pressure amplitude of the positive part of the cycle should be above 1.0 and its duration is below 1-3 microseconds.

The treatment depth can vary from the surface to the full depth of the human or animal torso and the treatment site can be defined by a much larger treatment area than the 0.10-3.0 $cm^2$ commonly produced by focused waves. The above methodology is particularly well suited for surface as well as sub-surface soft tissue treatments in one or more reflexology zones or to one or more reflexology zones and to an area near the source of the pain.

An exemplary treatment protocol could have emitted shock waves in a broad range of 0.01 $mJ/mm^2$ to 3.0 $mJ/mm^2$ and 200-2500 pulses per treatment with a treatment schedule of 1-3 weekly treatments until symptoms reduce. This can be repeated as symptoms reoccur or continue weekly as a preventative. The post medical treatment is beneficial as a pain suppressor and reduces the need for pain medications and allows less addictive medications to be used to prevent addiction. In other treatment protocols, the emitted shock waves or pressure pulses can employ as few as 1 to as high as 100,000 pulses per treatment.

The above methodology is valuable in generation of tissue, vascularization and may be used in combination with stem cell therapies as well as regeneration of tissue and vascularization.

The following invention description first provides a detailed explanation of acoustic shock waves or pressure pulses, as illustrated in FIGS. 1-9. As used herein an acoustic shock wave is an asymmetric wave with an exceptionally rapid peak rise time and slower return time from the peak amplitude. Historically, these acoustic shock waves or pressure pulses were first used medically to destroy kidney stones. The wave patterns were directed to a focal point with ah a relatively high energy to blast the concrements into small urinary tract passable fragments.

A whole class of acoustic shock waves or pressure pulses for medical treatments were later discovered that employed low energy acoustic shock waves or pressure pulses. These low energy acoustic shock waves or pressure pulses maintained the asymmetric wave profile, but at much lower energies as described in US2006/0100550 which is incorporated herein in its entirety.

These low energy acoustic shock waves or pressure pulses advantageously could stimulate a substance without requiring a focused beam. The advantage of such an unfocused beam was the acoustic wave could be directed to pass through tissue without causing any cell rupturing which would be evidenced by a lack of a hematoma or bruising. This use of unfocused, low energy acoustic shock waves or pressure pulses provided an ability to treat a large volume of tissue virtually painlessly. Furthermore, the acoustic energy caused a short duration anesthetic sensation that effectively numbs the patient's pain over a period of days with a prolonged reduction in pain thereafter.

The use of low energy acoustic shock waves or pressure pulses that employ a focused beam has been spurred on as a viable alternative to the unfocused low energy shock waves because the focal point being of a small point of energy has little or a small region of cell damage as the remaining portions of the wave pattern can provide a stimulating effect similar to the unfocused shock waves. Basically, the effect is the same with the users of focused waves achieving the benefits of the unfocused waves, but with a focal point of peak energy in a tiny localised region. So, for purposes of the present invention, the use of "soft waves" those defined by low energy beams will be applicable to both focused and unfocused beams o acoustic shock waves or pressure pulses for the present invention.

One last and significant point that the reader must appreciate is that an "acoustic shock wave" is not an "ultrasound wave". Sonic or ultrasound waves are generated with a uniform and symmetrical wave pattern similar to a sinusoidal wave. This type of sonic wave causes a sheer action on tissue as evidenced by a generation of heat within the tissue, for this reason, the use of sonic waves of the ultrasonic type are not considered as efficient in cell survivability rates.

The present preferred invention avoids the use of such cell damaging sonic waves, most particularly in treating glands, bone structures or nerves via a targeted reflexology zone.

With reference to FIGS. 1-9, a variety of schematic views of acoustic shock waves or pressure pulses are described. The following description of the proper amplitude and pressure pulse intensities of the shock waves 200 are provided below along with a description of how the shock waves actually function and have been taken from the co-pending application of the present inventors and replicated herein as described below. For the purpose of describing the shock waves 200 were used as exemplary and are intended to include all of the wave patterns discussed in the figures as possible treatment patterns.

FIG. 1 is a simplified depiction of a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17, a water cushion or any other kind of exit window for the acoustical energy is located.

Figure 2:
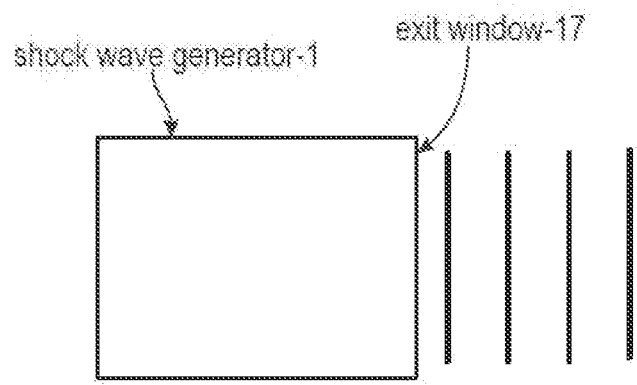
FIG. 2 is a simplified depiction of a pressure pulse I shock wave or pressure pulse generator with plane wave characteristics.

FIG. 2 is a simplified depiction of a pressure pulse/shock wave or pressure pulse generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 3:
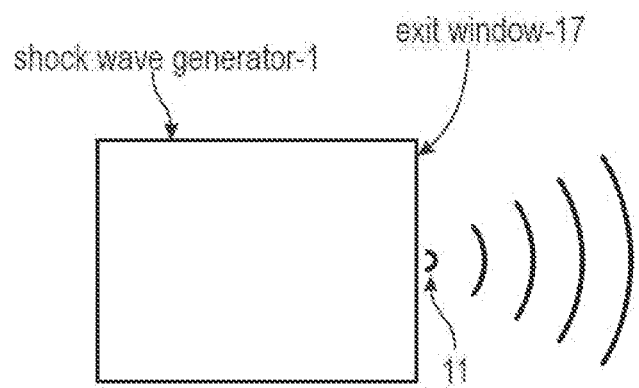
FIG. 3 is a simplified depiction of a pressure pulse I shock wave or pressure pulse generator with divergent wave characteristics.

FIG. 3 is a simplified depiction of a pressure pulse shock wave or pressure pulse generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1e the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup.

This apparatus, in certain embodiments, may be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the various types of acoustic shock waves or pressure pulses and types of shock wave generating heads provides versatility, the person skilled in the art will appreciate that apparatuses that produce low energy or soft acoustic shock waves or pressure pulses having, for one example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 4A:
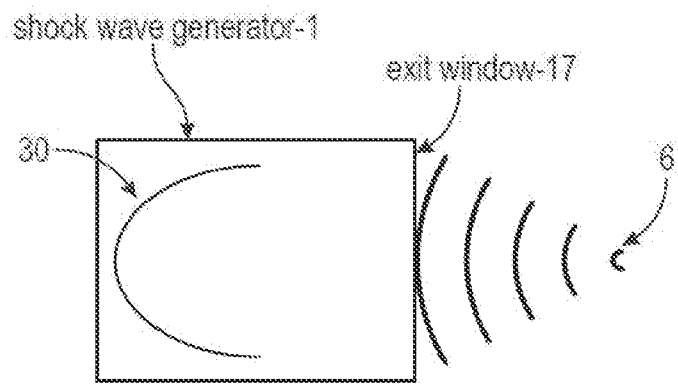
FIG. 4a is a simplified depiction of a pressure pulse/shock wave or pressure pulse generator having a focusing element in the form of an ellipsoid. The waves generated are focused.

FIG. 4a is a simplified depiction of the pressure pulse/shock wave or pressure pulse generator (shock wave head) having as focusing element an ellipsoid (30). Thus, the generated waves are focused at (6).

Figure 4B:
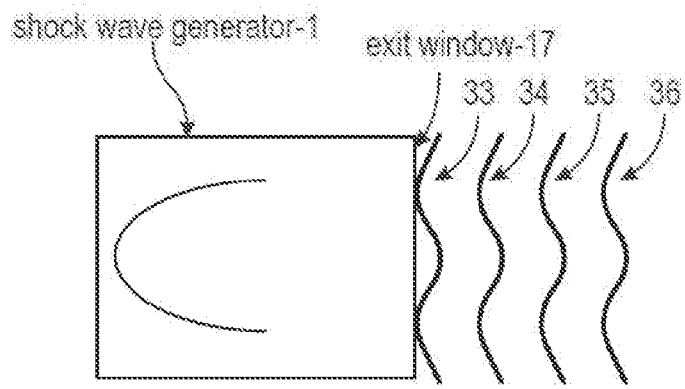
FIG. 4b is a simplified depiction of a pressure pulse/shock wave or pressure pulse generator having a parabolic reflector element and generating waves that are disturbed plane.

FIG. 4b is a simplified depiction of the pressure pulse/shock wave or pressure pulse generator (shock wave head) having as a focusing element an paraboloid (y2=2px). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
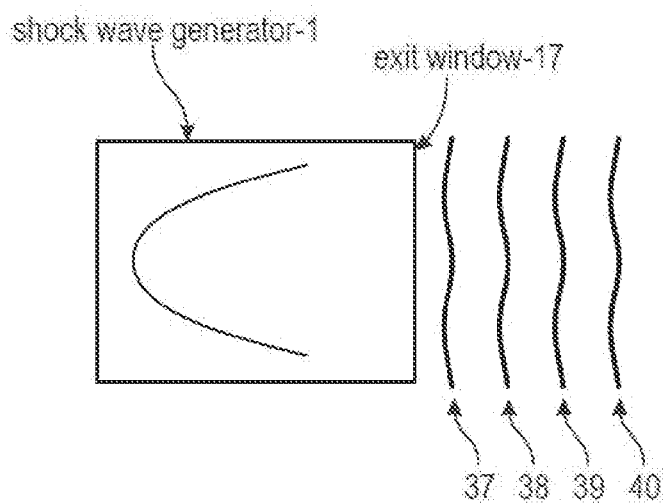
FIG. 4c is a simplified depiction of a pressure pulse/shock wave or pressure pulse generator having a quasi parabolic reflector element (generalized paraboloid) and generating waves that are nearly plane/have nearly plane characteristics.

FIG. 4c is a simplified depiction of the pressure pulse/shock wave or pressure pulse generator (shock wave head) having as a focusing element a generalized paraboloid (yn=2px, with 1.2<n<2.8 and n i–2). Thus, the characteristics of the wave fronts generated behind the exit window (37, 38, 39, and 40) are, compared to the wave fronts generated by a paraboloid (y2=2px), less disturbed, that is, nearly plane (or nearly parallel or nearly even (37, 38, 39, 40)). Thus, conformational adjustments of a regular paraboloid (y2=2px) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid (y2=2px) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
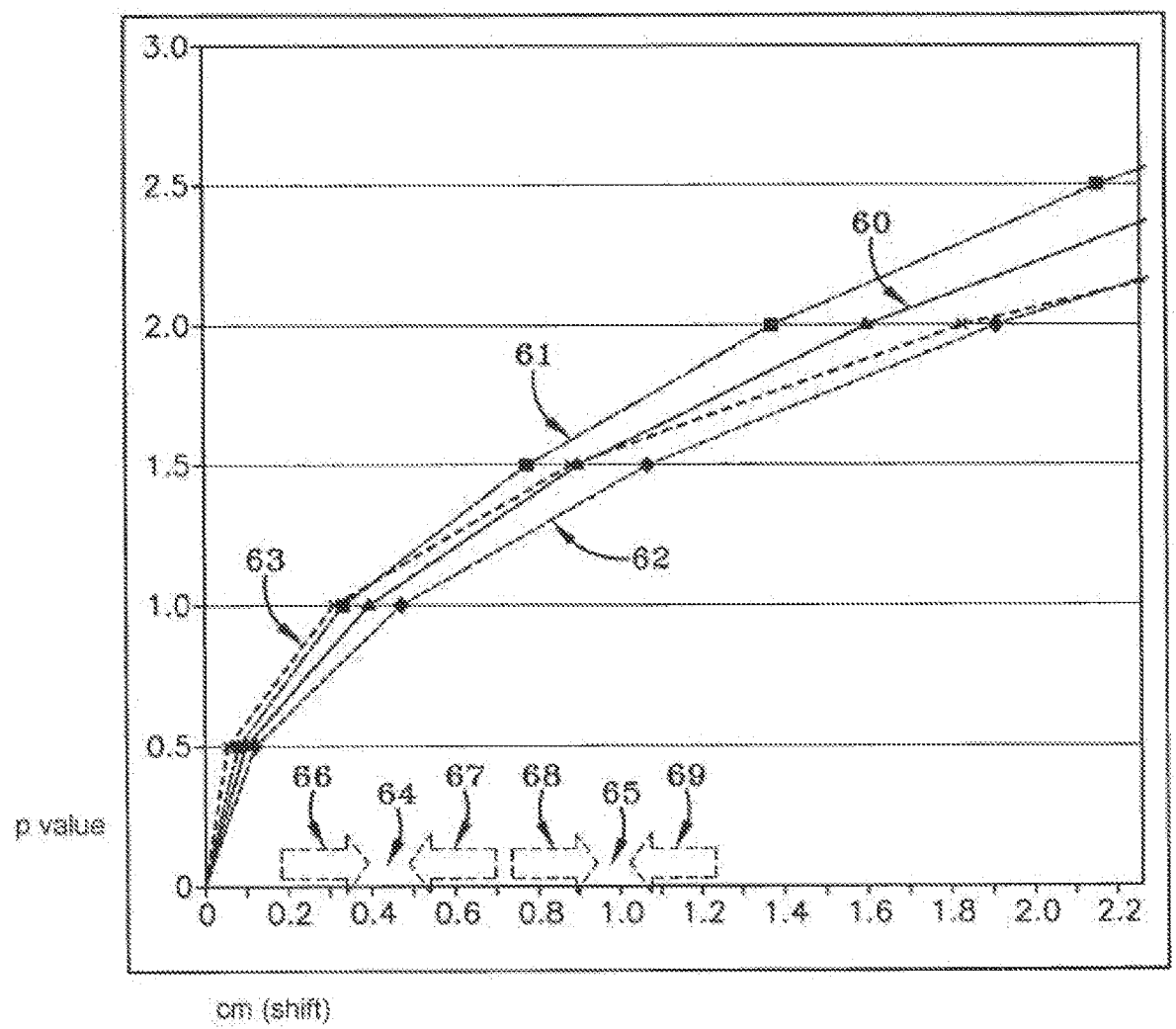
FIG. 4d is a simplified graphic depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape y2=2px with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicated by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of n cf. 2 and a p value of about 1.55 cm. The generalized paraboloid compensates for different p values that result from the electrode burn down and/or adjustment of the electrode tips.

Figure 5:
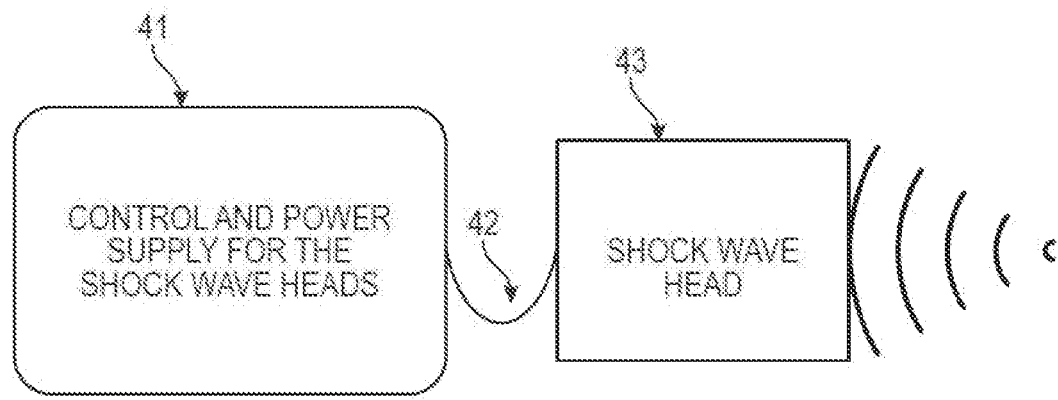
FIG. 5 is a simplified depiction of a pressure pulse/shock wave or pressure pulse generator being connected to a control/power supply unit.

FIG. 5 is a simplified depiction of a set-up of the pressure pulse/shock wave or pressure pulse generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
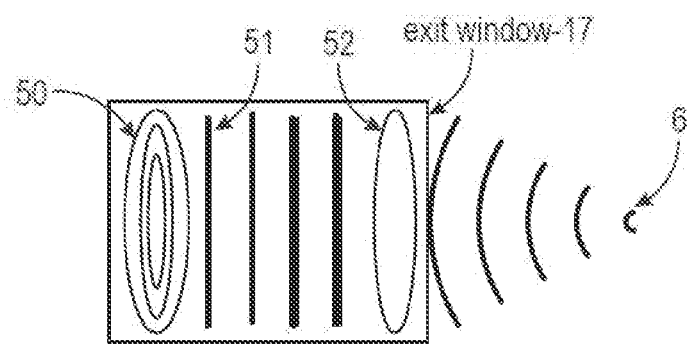
FIG. 6 is a simplified depiction of a pressure pulse/shock wave or pressure pulse generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave or pressure pulse generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
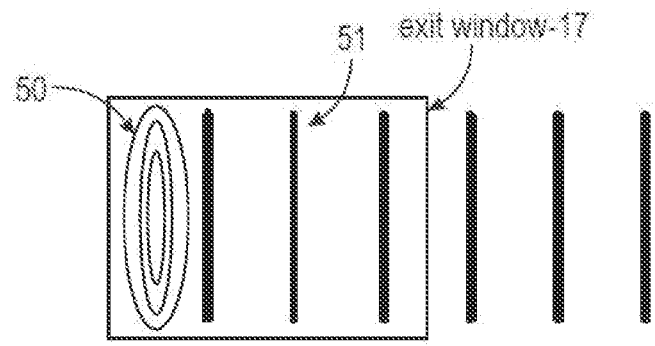
FIG. 7 is a simplified depiction of a pressure pulse/shock wave or pressure pulse generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave or pressure pulse generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
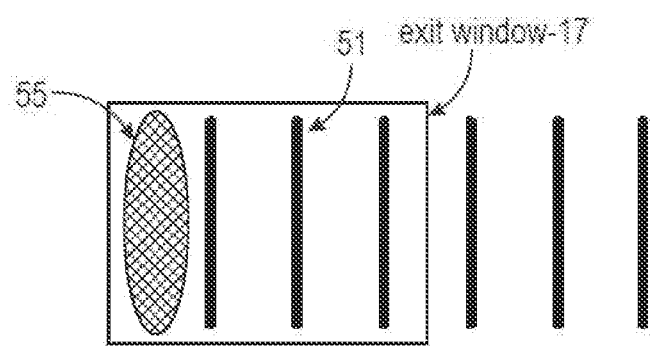
FIG. 8 is a simplified depiction of a pressure pulse/shock wave or pressure pulse generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave or pressure pulse generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
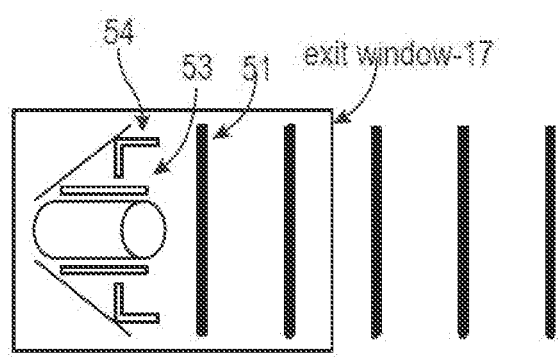
FIG. 9 is a simplified depiction of a pressure pulse/shock wave or pressure pulse generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/ shock wave or pressure pulse generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
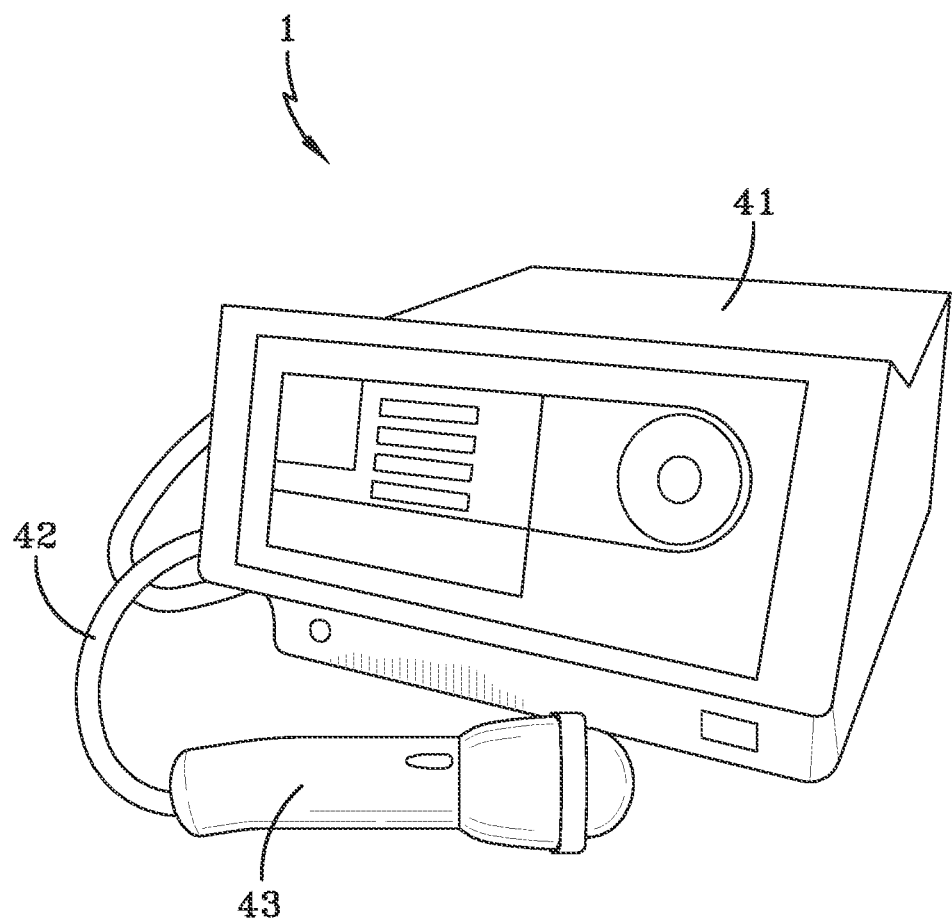
FIG. 10 shows an exemplary shock wave or pressure pulse generator device.

FIG. 10 shows an exemplary shock wave device generator or source 1 with a control and power supply 41 connected to a hand-held applicator shock wave head 43 via a flexible hose 42 with fluid conduits. The illustrated shock wave applicator 43 has a flexible membrane at an end of the applicator 43 which transmits the acoustic waves when coupled to the skin by using a fluid or acoustic gel. As shown, this type of applicator 43 has a hydraulic spark generator using either focused or unfocused shock waves, preferably in a low energy level, less than the range of 0.01 mJ/mm$^2$ to 0.3 mJ/mm$^2$. The flexible hose 42 is connected to a fluid supply that fills the applicator 43 and expands the flexible membrane when filled. Alternatively, a ballistic, piezoelectric or spherical acoustic shock wave device can be used to generate the desired waves.

Figure 11:
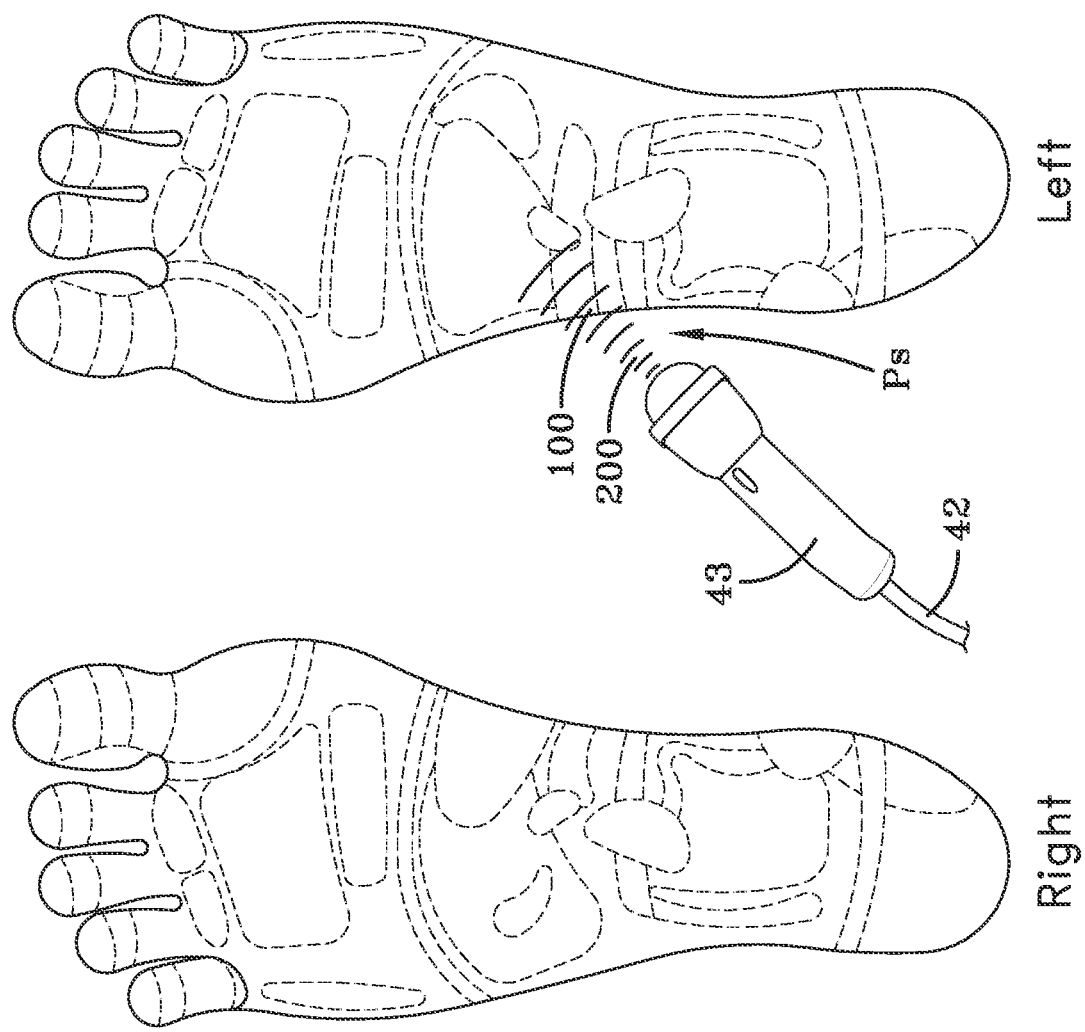
FIG. 11 shows the shock wave or pressure pulse generator device directed at one or more reflexology zones or to one or more reflexology zones and to an area near the source of the pain on a foot of a patient.

FIG. 11 is a perspective view of a foot of a patient whose reflexology zone or target 100 is being treated. A shock wave applicator head 43 is brought into contact with the skin Ps preferably an acoustic gel is used to enhance the transmission of the shock waves 200 through the skin Ps. The shock wave applicator head 43 can be hand held and manipulated across the skin Ps to drive the shock waves 200 in the direction the shock wave head 43 is pointed to activate a stimulating response through the reflexology zone 100. As illustrated, the device shown is an electrohydraulic acoustic shock wave or pressure pulse generator, however, other devices that generate acoustic shock waves or pressure pulses can be used. Ultrasonic devices may be considered, but there is no data to support a sinusoidal wave form would work and therefore not considered as effective as the asymmetric wave generators. The acoustic shock waves or pressure pulses activate a cellular response within the reflexology treatment site. This response or stimulation causes an increase of nitric oxide and a release of a variety of growth factors such as VEGF. As shown, the flexible membrane is protruding outward and the applicator 43 has been filled with fluid, the transmission or emission of acoustic shock waves or pressure pulses 200 is directed towards the reflexology zone 100. In order to accomplish a good transmission, it is important the flexible membrane be pressed against the patient's skin Ps and as indicated coupling gels may be used. The zone 100, as illustrated, is the reflexology zone for a bone structure which is a region of the foot located along an outside arch of each foot. By transmitting the shock waves 200 to the zone 100, is it believed that a modulation of the pain near the bone structure can be made. This modulation or adjustment is achieved by transmitting the acoustic waves 200 at low energy directly onto the zone 100. It is believed that a single treatment of the zone 100 will achieve the desired modulation. However, repeated treatments may be administered to help maintain and control this reduced pain level. Having achieved a scheduled pattern of treatments, it is possible to achieve regulation of pain without the use of drugs or other stimulants.

Figure 12:
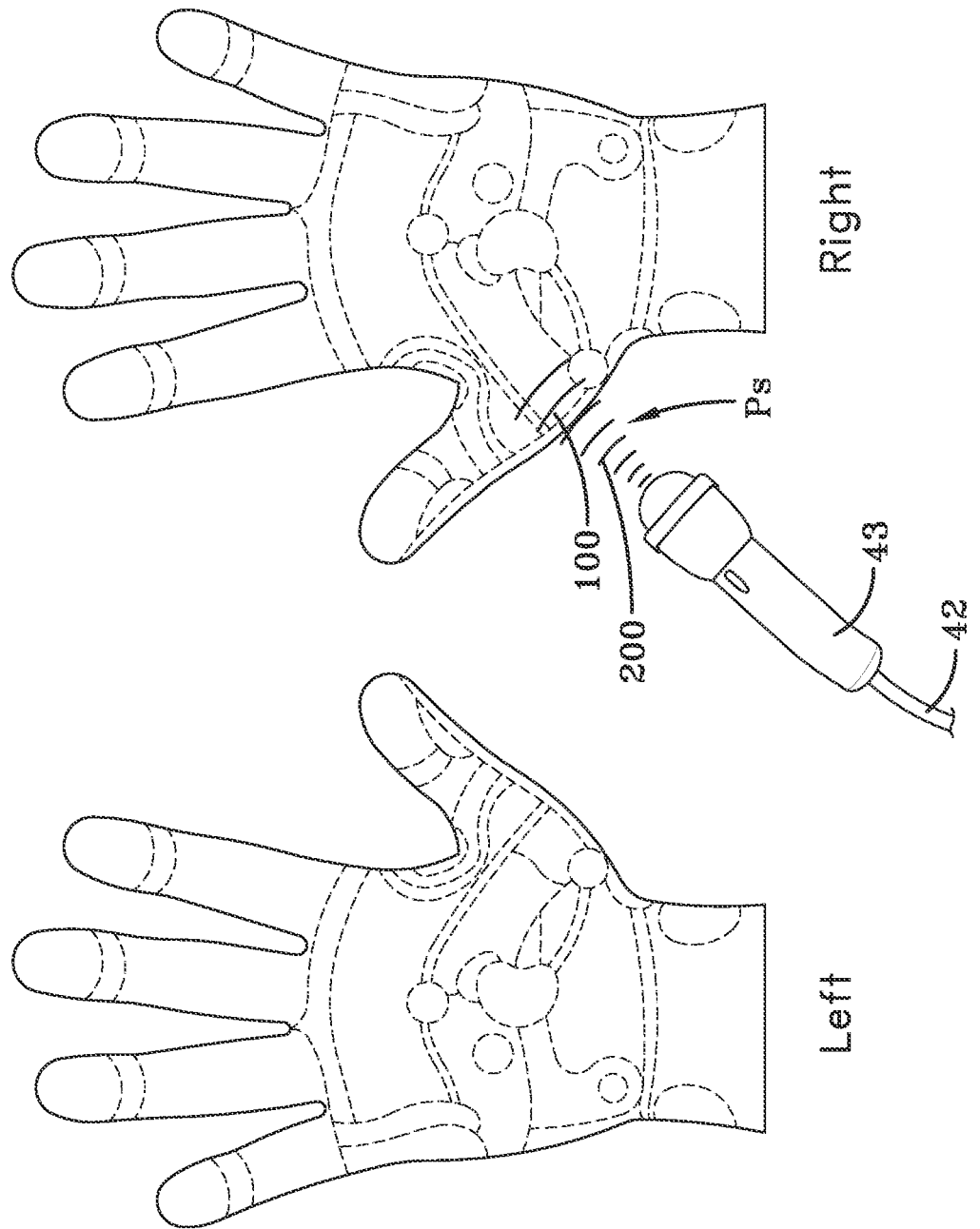
FIG. 12 shows the shock wave or pressure pulse generator device directed at one or more reflexology zones or to one or more reflexology zones and to an area near the source of the pain on a hand of a patient.

With reference to FIG. 12, a view of a hand of a patient whose reflexology zone 100 is being treated with acoustic shock waves or pressure pulses 200 is illustrated. In this illustration, it is important to note that the applicator 43 presses against the skin Ps of the hand in the reflexology zone 100 for the pancreas which is a region of the right hand in the fatty part below the index finger and a region of the left hand below the middle finger close to the wrist.

Figure 13:
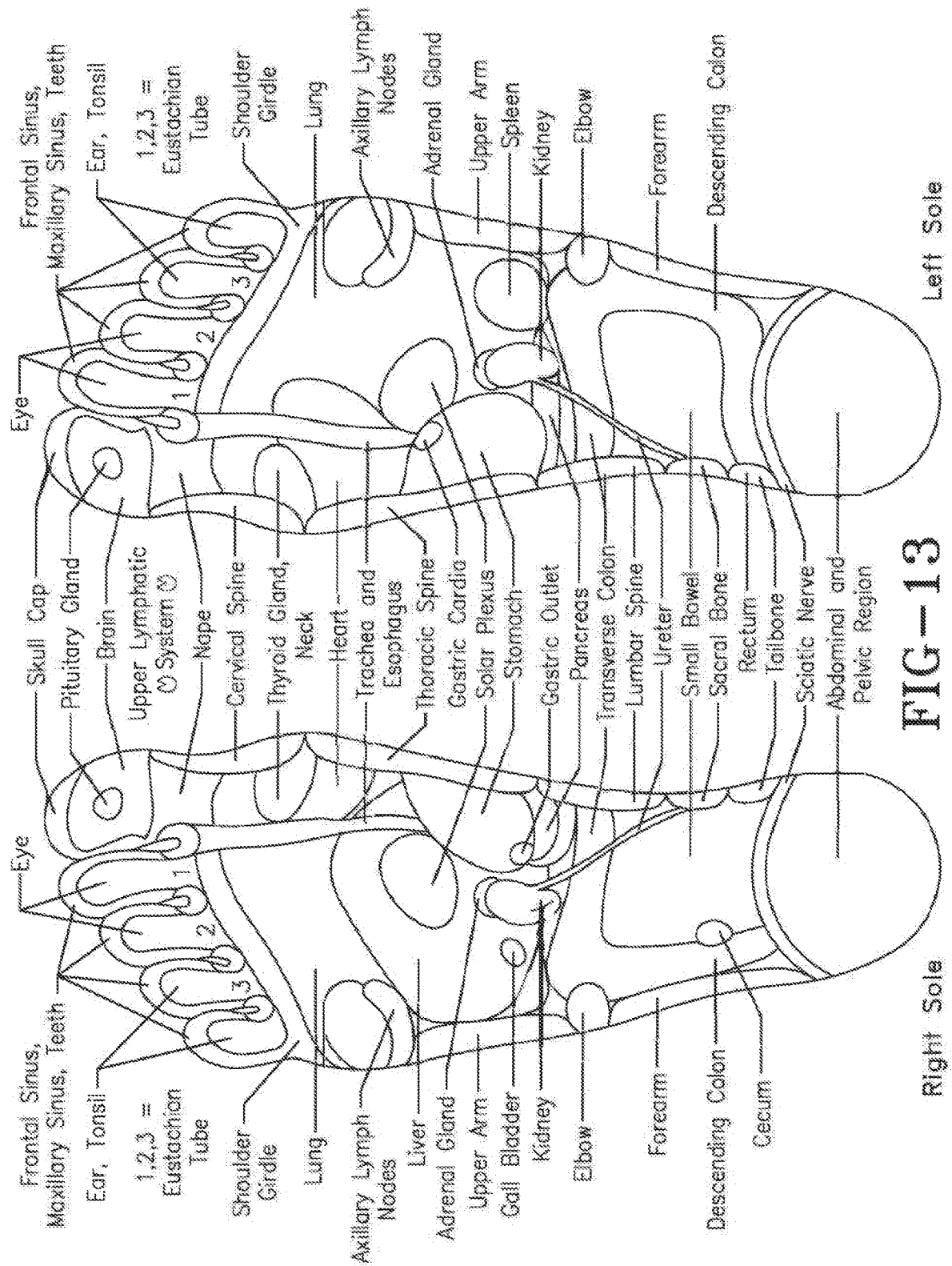
FIGS. 13-13C show schematic views showing general reflexology locations of the foot and ankle area in the human body.
Figure 13A:
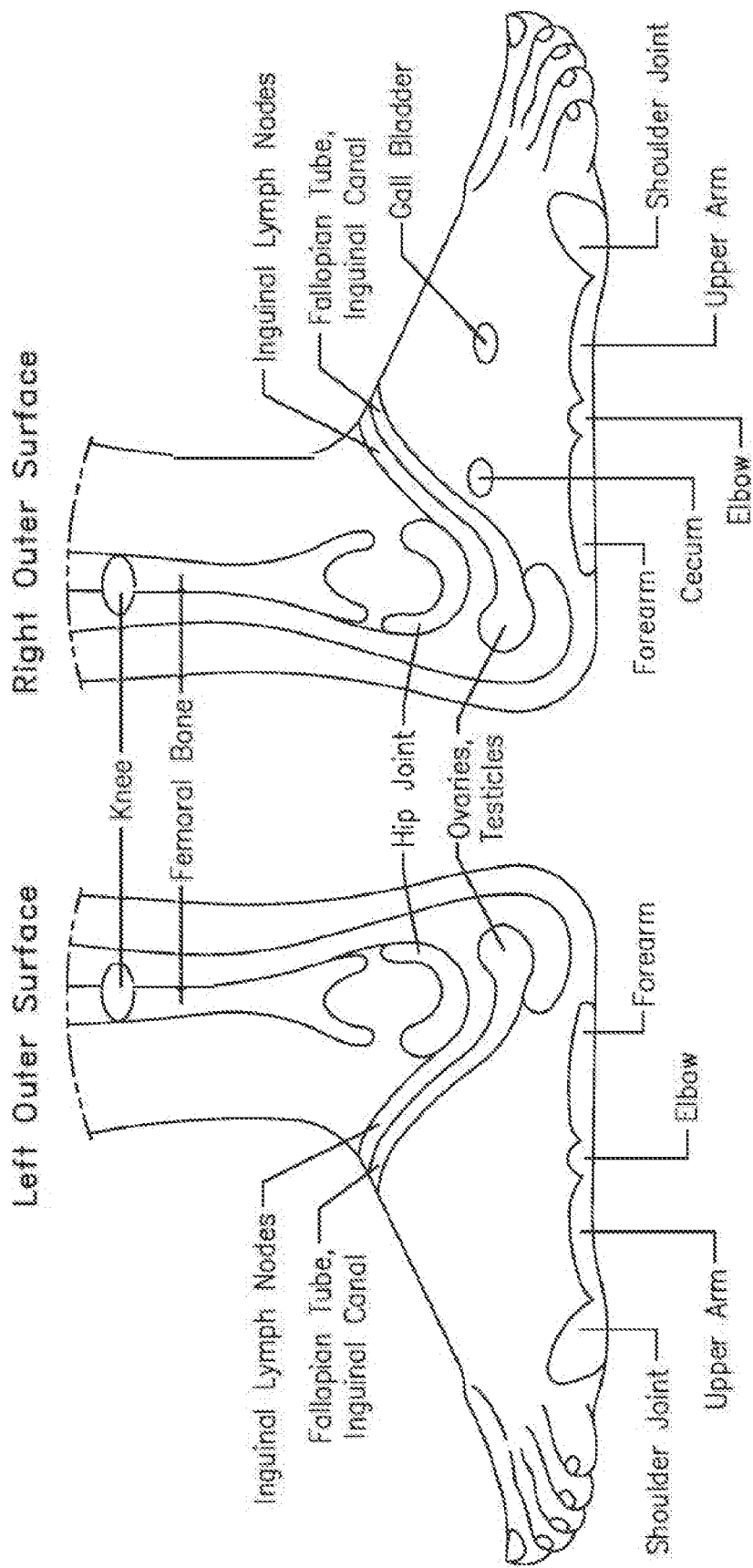
Figure 13B:
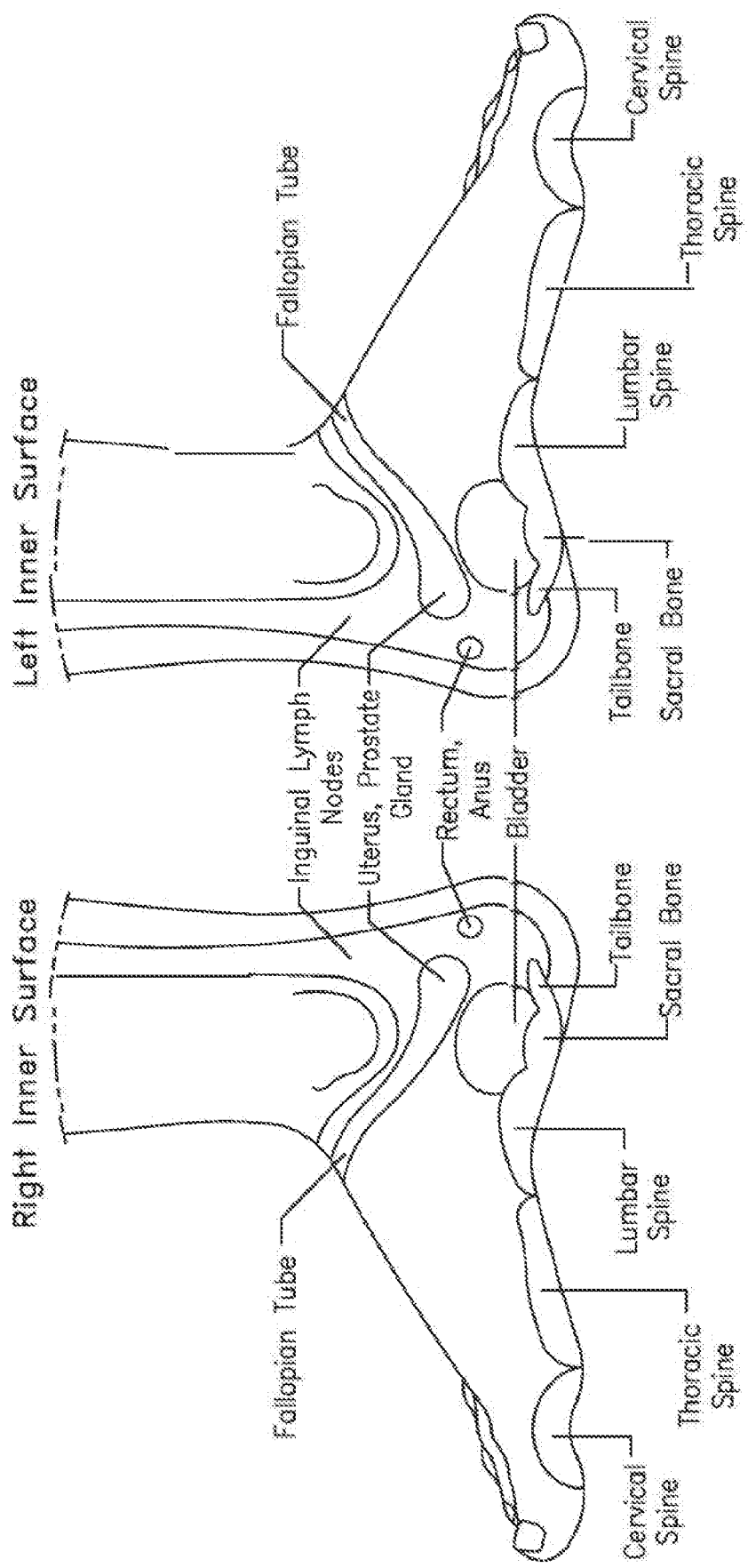
Figure 13C:
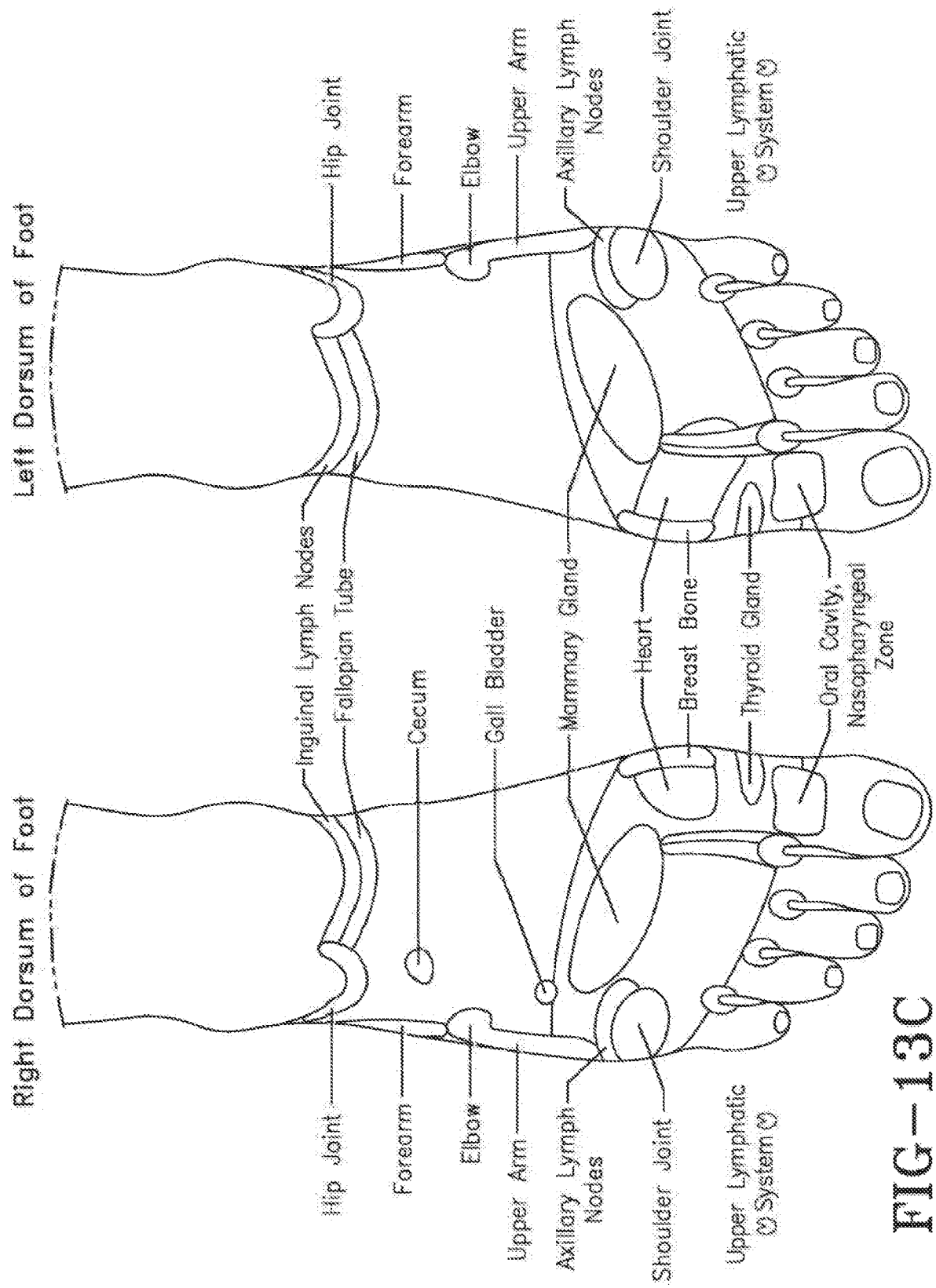

With reference to FIGS. 13-13C, reflexology foot and ankle area charts are shown detailing the various zones that correspond to organs, nerves, bones or glands of the body.

Figure 14:
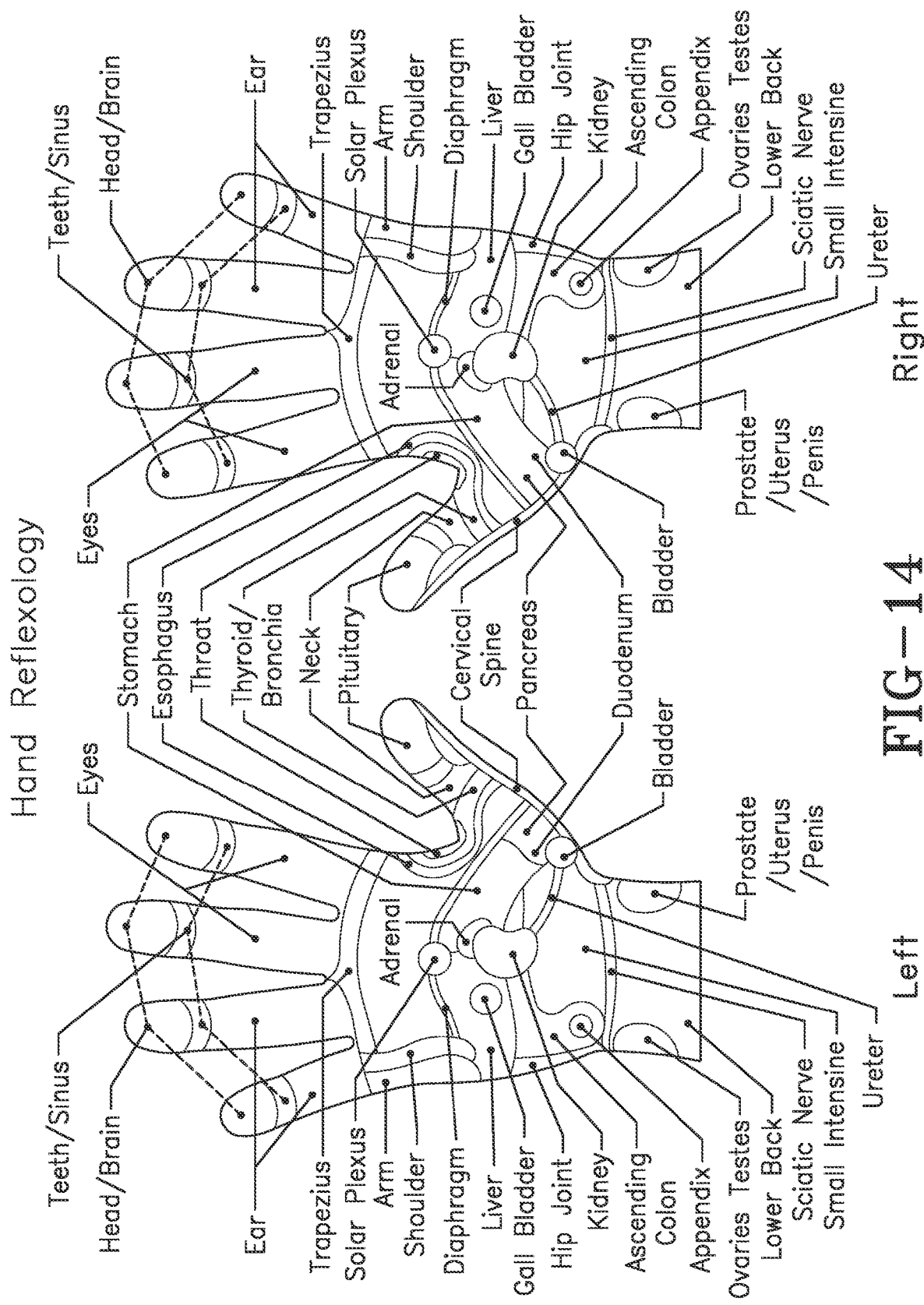
FIG. 14 shows a schematic view showing general reflexology locations of the hand in the human body.

With reference to FIG. 14, a reflexology hand chart is shown detailing the various zones that correspond to organs, nerves, bones or glands of the body.

The transmission of the shock waves 200 is preferred of a low energy density of 0.2 mJ/mm$^2$ whether using focused or unfocused shock waves. The acoustic shock waves or pressure pulses pulse rapidly through the cells penetrating the cell membrane extremely rapidly due to the rapid rise to peak time and pass through exiting slower due to the slower return from peak amplitude. This asymmetric wave pattern rapidly compresses each cell on entry and slow decompresses the cell as it exits. This effective squeezing of each cell is believed to cause the release of growth factors such as VEGF and others and also creates nitric oxide, all beneficial to new blood vessel formation. This occurs as a transmission across the cell membranes without rupturing the native cells.

Furthermore, such acoustic shock wave forms can be used in combination with drugs, chemical treatments, irradiation therapy or even physical therapy and when so combined the stimulated cells will more rapidly assist the body's natural healing response and thus overcomes the otherwise potentially tissue damaging effects of these complimentary procedures.

The present invention provides an apparatus for an effective treatment of indications, which benefit from high or low energy pressure pulse/shock waves having focused or unfocused, nearly plane, convergent or even divergent characteristics. With an unfocused wave having nearly plane, plane, convergent wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm$^2$ or even as low as 0.00 001 mJ/mm$^2$. In a preferred embodiment, those low end values range between 0.1-0.01 mJ/mm$^2$. With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output. Nevertheless, in some cases the first use of a high energy focused shock wave targeting a treatment zone may be the best approach followed by a transmission of lower energy unfocused wave patterns.

In the use of reflexology zones as the pathway or gate to control pain response, the present invention has actual empirical data showing the effectiveness in the zone directed to a bone. It is therefore further believed that similar modulation and beneficial adjustment can be achieved at other reflexology zones for stimulating, modulating or adjusting other glands, bones, nerves or organs such as the liver, kidney or any of those indicated in FIG. 13 for the foot zones and FIG. 14 for the hand zones. It is further believed that the hybrid Eastern medical acupuncture treatments or massages historically used are far less effective and less reliable than the results achieved by the deeper tissue penetrating transmission that are achieved by acoustic shock wave therapy applied to these reflexology zones. Historically, the inventor initially targeted treatment locations at the organ as in the patent U.S. Pat. No. 7,988,648 B2, but the present invention has found the use of the reflexology zones has achieved unexpected far superior results.

In the opioid or drug addition of the present invention, the inventors have been able to prevent opioid addiction by treating a surgical site immediately before surgery, or immediately after (up to 24 hours after) surgery. Additionally, in conjunction with above, or independently if the surgical wound is treated at the first and second office visit post-surgery addictive pain meds can be avoided. These surgical and post-surgical treatments can greatly reduce the opioid addictions created surgically every year, estimated to be at over 2 million Additionally, serious traumas, those not requiring surgery, if treated as soon as possible after the trauma, and continually on a daily or weekly basis until pain has subsided, will not require substantial pain medication. Shock wave or pressure pulse treatment replaces serious pain meds and or opioids. Additionally, the treatment helps a patient avoid or minimize withdrawal symptoms by treating their acute or chronic pain, and or by treating all of their reflexology zones on a weekly basis until symptoms subside. This is partly due to modulating hormone releases from the glands including the adrenal gland. The adrenals can also be targeted directly to enhance the effect to modulate withdrawal symptoms.

There are two main groups of adrenoreceptors, $\alpha$ and $\beta$, with 9 subtypes in total: $\alpha$ are divided to $\alpha 1$ (a Gq coupled receptor) and $\alpha 2$ (a Gi coupled receptor); $\alpha 1$ has 3 subtypes: $\alpha 1A$, $\alpha 1B$ and $\alpha 1D$; $\alpha 2$ has 3 subtypes: $\alpha 2A$, $\alpha 2B$ and $\alpha 2C$; $\beta$ are divided to $\beta 1$, $\beta 2$ and $\beta 3$. All 3 are coupled to Gs proteins, but $\beta 2$ and $\beta 3$ also couple to Gi. Gi and Gs are linked to adenylyl cyclase. Agonist binding thus causes a rise in the intracellular concentration of the second messenger cAMP. Gi inhibits the production of cAMP. Downstream effectors of cAMP include cAMP-dependent protein kinase (PKA), which mediates some of the intracellular events following hormone binding. Epinephrine (adrenaline) reacts with both $\alpha$- and $\beta$-adrenoreceptors, causing vasoconstriction and vasodilation, respectively. Although a receptors are less sensitive to epinephrine, when activated at pharmacologic doses, they override the vasodilation mediated by $\beta$-adrenoreceptors because there are more peripheral $\alpha 1$ receptors than $\beta$-adrenoreceptors. The result is that high levels of circulating epinephrine cause vasoconstriction. However, the opposite is true in the coronary arteries, where $\beta 2$ response is greater than that of $\alpha 1$, resulting in overall dilation with increased sympathetic stimulation. At lower levels of circulating epinephrine (physiologic epinephrine secretion), $\beta$-adrenoreceptor stimulation dominates since epinephrine has a higher affinity for the $\beta 2$ adrenoreceptor than the $\alpha 1$ adrenoreceptor, producing vasodilation followed by decrease of peripheral vascular resistance. Smooth muscle behavior is variable depending on anatomical location. One important note is the differential effects of increased cAMP in smooth muscle compared to cardiac muscle. Increased cAMP will promote relaxation in smooth muscle, while promoting increased contractility and pulse rate in cardiac muscle.

$\alpha$ receptors have actions in common, but also individual effects. Common or still receptor unspecified actions include: vasoconstriction and decreased motility of smooth muscle in gastrointestinal tract. Subtype unspecific $\alpha$ agonists can be used to treat rhinitis, they decrease mucus secretion. Subtype unspecific a antagonists can be used to treat pheochromocytoma, they decrease vasoconstriction caused by norepinephrine.

$\alpha 1$-adrenoreceptors are members of the Gq protein-coupled receptor superfamily. Upon activation, a heterotrimeric G protein, Gq, activates phospholipase C (PLC). The PLC cleaves phosphatidylinositol 4,5-bisphosphate (PIP2), which in turn causes an increase in inositol triphosphate (IP3) and diacylglycerol (DAG). The former interacts with calcium channels of endoplasmic and sarcoplasmic reticulum, thus changing the calcium content in a cell. This triggers all other effects, including a prominent slow after depolarizing current (sADP) in neurons. Actions of the a1 receptor mainly involve smooth muscle contraction. It causes vasoconstriction in many blood vessels, including those of the skin, gastrointestinal system, kidney, renal artery, and brain. Other areas of smooth muscle contraction are: ureter, vas deferens, hair (arrector pili muscles), uterus (when pregnant), urethral sphincter, urothelium and lamina propria, bronchioles (although minor relative to the relaxing effect of $\beta 2$ receptor on bronchioles), blood vessels of ciliary body (stimulation causes mydriasis). Actions also include glycogenolysis and gluconeogenesis from adipose tissue and liver; secretion from sweat glands and Na+ reabsorption from kidney. $\alpha 1$ antagonists can be used to treat: hypertension, they decrease blood pressure by decreasing peripheral vasoconstriction and benign prostate hyperplasia, they relax smooth muscles within the prostate thus easing urination.

The $\alpha 2$ receptor couples to the Gi/o protein. It is a presynaptic receptor, causing negative feedback on, for example, norepinephrine (NE). When NE is released into the synapse, it feeds back on the $\alpha 2$ receptor, causing less NE release from the presynaptic neuron. This decreases the effect of NE. There are also $\alpha 2$ receptors on the nerve terminal membrane of the post-synaptic adrenergic neuron. Actions of the $\alpha 2$ receptor include: decreased insulin release from the pancreas, increased glucagon release from the pancreas, contraction of sphincters of the GI-tract, negative feedback in the neuronal synapses-presynaptic inhibition of norepinephrine release in CNS, increased platelet aggregation (increased blood clotting tendency), decreases peripheral vascular resistance. $\alpha 2$ agonists can be used to treat: hypertension, they decrease blood pressure raising actions of the sympathetic nervous system, impotence, they relax penile smooth muscles and ease blood flow and depression, they enhance mood by increasing norepinephrine secretion.

Subtype unspecific $\beta$ agonists can be used to treat: heart failure, they increase cardiac output acutely in an emergency, circulatory shock, they increase cardiac output thus redistributing blood volume, and anaphylaxis-bronchodilation. Subtype unspecific $\beta$ antagonists, beta blockers, can be used to treat: heart arrhythmia, they decrease the output of sinus node thus stabilizing heart function, coronary artery disease, they reduce heart rate and hence increasing oxygen supply, heart failure, they prevent sudden death related to this condition, which is often caused by ischemias or arrhythmias, hyperthyroidism, they reduce peripheral sympathetic hyperresponsiveness, migraine, they reduce number of attacks, stage fright, they reduce tachycardia and tremor, glaucoma, they reduce intraocular pressure.

Actions of the $\beta 1$ receptor include: increase cardiac output by increasing heart rate (positive chronotropic effect), conduction velocity (positive dromotropic effect), stroke volume (by enhancing contractility-positive inotropic effect), and rate of relaxation of the myocardium, by increasing calcium ion sequestration rate (positive lusitropic effect), which aids in increasing heart rate; increase renin secretion from juxtaglomerular cells of the kidney and increase ghrelin secretion from the stomach.

β2 adrenoreceptor (PDB: 2rh1) stimulates cells to increase energy production and utilization. Actions of the β2 receptor include: smooth muscle relaxation throughout many areas the body, e.g. in bronchi (bronchodilation, see salbutamol), GI tract (decreased motility), veins (vasodilation of blood vessels), especially those to skeletal muscle (although this vasodilator effect of norepinephrine is relatively minor and overwhelmed by α adrenoceptor-mediated vasoconstriction), lipolysis in adipose tissue, anabolism in skeletal muscle, relax non-pregnant uterus, relax detrusor urinae muscle of bladder wall, dilate arteries to skeletal muscle, glycogenolysis and gluconeogenesis, stimulates insulin secretion, contract sphincters of GI tract, thickened secretions from salivary glands, inhibit histamine-release from mast cells, increase renin secretion from kidney, and involved in brain-immune communication. β2 agonists can be used to treat: asthma and COPD, they reduce bronchial smooth muscle contraction thus dilating the bronchus, hyperkalemia, they increase cellular potassium intake, and preterm birth, they reduce uterine smooth muscle contractions.

Actions of the β3 receptor include: increase of lipolysis in adipose tissue. β3 agonists could theoretically be used as weight-loss drugs, but are limited by the side effect of tremors.

Shock wave or pressure pulse treatment can modulate alpha 1 and 2, beta, and other adrenergic receptors by directly targeting the tissue AND by the stimulation of the reflexology zones. For example, by targeting the hearts reflexology zones you can modulate alpha receptors in the heart. Shock wave or pressure pulse treatment can recruit, activate and differentiate stem cells by directly targeting the pathologic tissue or by targeting the pertinent reflexology zones or preferably by doing both in combination. This is the same for modulating inflammation locally by the direct targeting or modulating SYSTEMIC inflammation by treating any or all of the reflexology zones.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a surgical patient who is or will be prescribed an opioid or non-opioid addictive pain medication to prevent opioid addiction comprises the step of:
    activating an acoustic shock wave generator to emit acoustic shock waves;
    treating the patient with the acoustic shock waves emitted by the acoustic shock wave generator, wherein the acoustic shock waves comprise a low pulse energy of 0.00001 mJ/mm$^2$ or higher up to 1.0 mJ/mm$^2$ and an amplitude above 0.1 MPa and rise times of the amplitude are below 100 nano-seconds with a duration of the acoustic shock waves being below 3 micro-seconds for a positive part of a cycle prior to surgery, during surgery, or up to two weeks after surgery, or any combination thereof to reduce post surgical pain such that the pain medication is avoided or drastically reduced; and
    the step of treating the patient with the acoustic shock waves comprising subjecting adrenal glands of the patient through a surface of a skin with the acoustic shock waves to modulate hormonal levels of the patient by reducing adrenalin and cortisol levels in order to prevent or minimize withdrawal symptoms from the opioid or non-opioid addictive pain medication.

2. The method of claim 1 further comprises treating an entire surgical area after surgery until pain has been resolved or reduced to a point where medications are not required.

3. The method of claim 1 wherein the acoustic shock waves are directed to one or more reflexology zones of the hands or feet for the purpose of reducing pain and accelerating healing.

4. The method of claim 3 wherein the acoustic shock waves are additionally directed to an area of the one or more reflexology zones directed to modulate a response to the pain to suppress urges to take the addictive medication or opioids and to prevent or minimize withdrawal symptoms from the opioid or non-opioid addictive pain medication; and further comprises the step of:
    recruiting, activating and differentiating stem cells by directly targeting an entire surgical area or by targeting the one or more reflexology zones or doing both.

* * * * *